US006133503A

United States Patent [19]
Scheffler

[11] Patent Number: 6,133,503
[45] Date of Patent: Oct. 17, 2000

[54] MAMMALIAN ARTIFICIAL CHROMOSOMES AND METHODS OF USING SAME

[75] Inventor: Immo E. Scheffler, Del Mar, Calif.

[73] Assignee: The Regents of the University of California, Oakland, Calif.

[21] Appl. No.: 09/024,472

[22] Filed: Feb. 17, 1998

Related U.S. Application Data

[62] Division of application No. 08/741,406, Oct. 29, 1996, Pat. No. 5,721,118.
[60] Provisional application No. 60/039,256, Oct. 31, 1995.

[51] Int. Cl.⁷ .................................................. C12N 15/00
[52] U.S. Cl. ................................ 800/21; 800/24; 800/25
[58] Field of Search ........................ 800/14–25; 435/455, 435/463, 449, 320.1, 325, 69.1

[56] References Cited

U.S. PATENT DOCUMENTS 5,288,625  2/1994  Hadlaczky ........................... 435/172.2

OTHER PUBLICATIONS

Brown et al., "Mammalian artificial chromosomes," *Current Opinion in Genetics Development*, 6:281–288 (1996).
Carine et al., "Chinese Hamster Cells with a Minichromosome Containing the Centromere Region of Human Chromosome 1" *Somat. Cell Mol. Gen.* 12:479–491 (1986).
Carine et al., "Molecular Characterization of Human Minichromosomes with Centromere from Chromosome 1 in Human Hamster Hybrid Cells" *Somat. Cell Mol. Gene.* 15:445–460 (1989).
Cochran et al., "The cDNA Sequence of Beef Heart CII–3, a Membrane–intrinsic Subunit of Succinate–ubiquinone Oxidoreductase" *Biochimica et Biophysica Acta* 1188:162–166 (1994).
Farr et al., "Generation of a Human X–derived Minichromosome Using Telomere–associated Chromosome Fragmentation" *EMBO J.* 14:5444–5454 (1995).
Heller et al., "Mini–chromosomes derived from the human Y chromosome by telomere directed chromosome breakage" *Proc. Nat'l. Acad. Sci. USA*, 93:7125–7130 (1996).
S. Henikoff, "Position–effect variegation after 60 years," *Trends in Genetics*, 6:422–426 (1990).
Huxley et al., "Ordering up Big MACS" *Bio/Technology* 12:586–590 (1994).
Huxley, "Transfer of YAC's to Mammalian Cells and Transgenic Mice" *Genetic Engineering* 16:65–91 (1994).
Jakobivits et al., "Germ–line Transmission and Expression of a Human–derived Yeast Artificial Chromosome" *Nature* 362:255–258 (1993).
Mascarello et al., "Assignment of a Gene for Succinate Dehydrogenase to Human Chromosome 1 by Somatic Cell Hybridization" *Cytogenetics Cell Genet.* 28:121–135 (1980).

Monaco and Larin, "YACs, BACs, PACs, and MACs: Artificial Chromosomes as Research Tools," *Trends in Biotechnology*, 12:280–286 (1994).
Montoliu et al., "Germ Line Transmission of Yeast Artificial Chromosomes in Transgenic Mice" *Reprod. Fertility & Devel.* 6:577–584 (1994).
Oostveen et al., "A Chinese Hamster Mutant Cell Line with a Defect in the Integral Membrane Protein CII–3 of Complex II of the Mitochondrial Electron Transport Chain" *J. Biol. Chem.* 270:26104–26108 (1995).
Solus et al., "Characterization of Single–Copy Probe from Vicinity of Centromere of Human Chromosome 1," *Somat. Cell Mol. Genet.*, 14:381–391 (1988).
H. F. Willard, "Chromosome manipulation: A systematic approach toward understanding human chromosome structure and function," *Proc. Nat'l. Acad. Sci. USA* 93:6847–6850 (1996).
Jiewen et al., Theriogenology, vol. 45, No. 1, p. 336, Jan. 1, 1996.
Moreadith et al., J. Mol. Med., vol. 75, pp. 208–216, 1997.
Seamark, Reprod. Fertil. Dev., vol. 6, pp. 653–657, 1994.
Mullins et al., J. Clin. Invest., vol. 98, No. 11, pp. S37–S40, 1996.
Wall, Theriogenology, vol. 45, pp. 57–68, 1996.
Kappel et al., Current Opinion in Biotechnology, vol. 3, pp. 548–553, 1992.
Strojek & Wagner, Genetic Engineering: Principles and Methods, vol. 10, pp. 221–246, 1988.
Hammer et al., J. Anim. Sci., vol. 63, pp. 269–278, 1986.
Brown et al., Current Opinion in Genetics and Development, vol. 6, pp. 281–288, 1996.
Henikoff, Trends in Genetics, vol. 6, pp. 422–426, Dec. 1990.
Monaco et al., Trends in Biotechnology, vol. 12, pp. 280–286, Jul. 1994.

*Primary Examiner*—Bruce R. Campell
*Assistant Examiner*—Joseph Woitach
*Attorney, Agent, or Firm*—Campbell & Flores LLP

[57] ABSTRACT

The present invention provides a mammalian artificial chromosome (MAC), comprising a centromere and a unique cloning site, said MAC containing less than 0.1% of the DNA present in a normal haploid genome of the mammalian cell from which the centromere was obtained. The invention further provides a MAC, wherein the unique cloning site is a nucleic acid sequence encoding a selectable marker. The invention also provides methods of preparing a MAC. In addition, the invention provides methods of stably expressing a selectable marker in a cell, comprising introducing a MAC containing the selectable marker into the cell. The invention also provides a cell containing a MAC expressing an exogenous nucleic acid sequence and a transgenic mammal expressing a selectable marker.

14 Claims, 3 Drawing Sheets

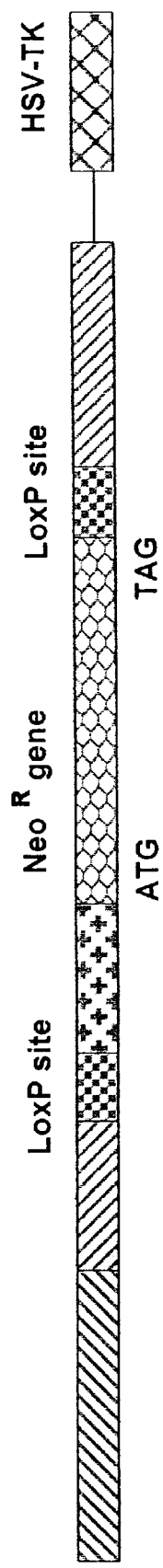
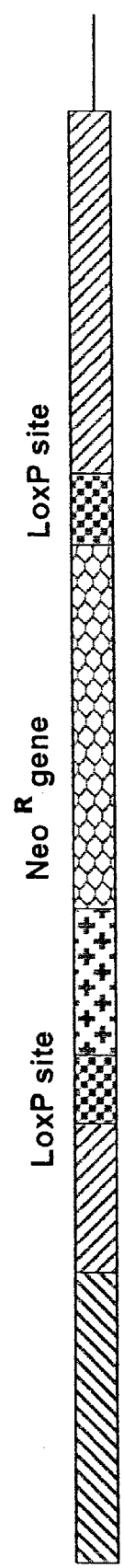
Figure 1a
Figure 1b
Figure 1c

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1315 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 27..536

(xi) SEQUENCE DESCRIPTION: SEQ ID NO:1:

```
ACTTCCGTTC CAGACCGGAA CCCAAG ATG GCT GCG CTG TTG CTG AGA CAC GTT        53
                            Met Ala Ala Leu Leu Leu Arg His Val
                             1               5

GGT CGT CAT TGC CTC CGA GCC CAC TTT AGC CCT CAG CTC TGT ATC AGA        101
Gly Arg His Cys Leu Arg Ala His Phe Ser Pro Gln Leu Cys Ile Arg
 10              15                  20                  25

AAT GCT GTT CCT TTG GGA ACC ACG GCC AAA GAA GAG ATG GAG CGG TTC        149
Asn Ala Val Pro Leu Gly Thr Thr Ala Lys Glu Glu Met Glu Arg Phe
                 30                  35                  40

TGG AAT AAG AAT ATA GGT TCA AAC CGT CCT CTG TCT CCC CAC ATT ACT        197
Trp Asn Lys Asn Ile Gly Ser Asn Arg Pro Leu Ser Pro His Ile Thr
             45                  50                  55

ATC TAC AGT TGG TCT CTT CCC ATG GCG ATG TCC ATC TGC CAC CGT GGC        245
Ile Tyr Ser Trp Ser Leu Pro Met Ala Met Ser Ile Cys His Arg Gly
         60                  65                  70

ACT GGT ATT GCT TTG AGT GCA GGG GTC TCT CTT TTT GGC ATG TCG GCC        293
Thr Gly Ile Ala Leu Ser Ala Gly Val Ser Leu Phe Gly Met Ser Ala
     75                  80                  85

CTG TTA CTC CCT GGG AAC TTT GAG TCT TAT TTG GAA CTT GTG AAG TCC        341
Leu Leu Leu Pro Gly Asn Phe Glu Ser Tyr Leu Glu Leu Val Lys Ser
 90                  95                 100                 105

CTG TGT CTG GGG CCA GCA CTG ATC CAC ACA GCT AAG TTT GCA CTT GTC        389
Leu Cys Leu Gly Pro Ala Leu Ile His Thr Ala Lys Phe Ala Leu Val
                110                 115                 120
```

```
TTC CCT CTC ATG TAT CAT ACC TGG AAT GGG ATC CGA CAC TTG ATG TGG         437
Phe Pro Leu Met Tyr His Thr Trp Asn Gly Ile Arg His Leu Met Trp
            125                 130                 135

GAC CTA GGA AAA GGC CTG AAG ATT CCC CAG CTA TAC CAG TCT GGA GTG         485
Asp Leu Gly Lys Gly Leu Lys Ile Pro Gln Leu Tyr Gln Ser Gly Val
            140                 145                 150

GTT GTC CTG GTT CTT ACT GTG TTG TCC TCT ATG GGG CTG GCA GCC ATG         533
Val Val Leu Val Leu Thr Val Leu Ser Ser Met Gly Leu Ala Ala Met
            155                 160                 165

TGAAGAAAGG AGGCTCCCAG CATCATCTTC CTACACATTA TTACATTCAC CCATCTTTCT       593

GTTTGTCATT CTTATCTCCA GCCTGGGAAA AGTTCTCCTT ATTTGTTTAG ATCCTTTTGT       653

ATTTTCAGAT CTCCTTGGAG CAGTAGAGTA CCTGGTAGAC CATAATAGTG GAAAAGGGTC       713

TAGTTTTCCC CTTGTTTCTA AAGATGAGGT GGCTGCAAAA ACTCCCCTTT TTTGCCCACA       773

GCTTGCCTAC TCTCGGCCTA GAAGCAGTTA TTCTCTCTCC ATATTGGGCT TTGATTTGTG       833

CTGAGGGTCA GCTTTTGGCT CCTTCTTCCT GAGACAGTGG AAACAATGCC AGCTCTGTGG       893

CTTCTGCCCT GGGGATGGGC CGGGTTGGGG GGTGGGTTGG GTGAAGCTTT GGGTTGCCAC       953

TGCCTGTGGG TTTGCTGGCT TAAAGGACAA TTCTCTTTCA TTGGTGAGAG CCCAGGCCAT      1013

TAACAACTAA CACAGTGTTA TTGAAAGAAG AGAGGTGGGG GTGGAGGGGA ATTAGTCTGT      1073

CCCAGCTAGA GGGAGATAAA GAGGGCTAGT TAGTTCTTGG AGCAGCTGCT TTTGAGGAGA      1133

AAATATATAG CTTTGGACAC GAGGAAGATC TAGAAAATTA TCATTGAACA TATTAATGGT      1193

TATTTCTTTT TCTTGGATTT CCAGAAAAGC CTCTTAATTT TATGCTTTCT CATCGAAGTA      1253

ATGTACCCTT TTTTTCTGAA ACTGAATTAA ATACTCATTT TAAAAAAAAA AAAAAAAAA       1313

AA                                                                    1315

(2) INFORMATION FOR SEQ ID NO:2:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ala Leu Leu Leu Arg His Val Gly Arg His Cys Leu Arg Ala
 1               5                  10                  15

His Phe Ser Pro Gln Leu Cys Ile Arg Asn Ala Val Pro Leu Gly Thr
                20                  25                  30

Thr Ala Lys Glu Glu Met Glu Arg Phe Trp Asn Lys Asn Ile Gly Ser
            35                  40                  45

Asn Arg Pro Leu Ser Pro His Ile Thr Ile Tyr Ser Trp Ser Leu Pro
        50                  55                  60

Met Ala Met Ser Ile Cys His Arg Gly Thr Gly Ile Ala Leu Ser Ala
 65                 70                  75                  80

Gly Val Ser Leu Phe Gly Met Ser Ala Leu Leu Pro Gly Asn Phe
                85                  90                  95

Glu Ser Tyr Leu Glu Leu Val Lys Ser Leu Cys Leu Gly Pro Ala Leu
                100                 105                 110

Ile His Thr Ala Lys Phe Ala Leu Val Phe Pro Leu Met Tyr His Thr
            115                 120                 125

Trp Asn Gly Ile Arg His Leu Met Trp Asp Leu Gly Lys Gly Leu Lys
        130                 135                 140
```

```
Ile Pro Gln Leu Tyr Gln Ser Gly Val Val Leu Val Leu Thr Val
145                 150                 155                 160

Leu Ser Ser Met Gly Leu Ala Ala Met
                165

(2) INFORMATION FOR SEQ ID NO:3:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (xi) SEQUENCE DESCRIPTION: SEQ ID NO:3:

TTCCCCATAC TCAGGAGGCT GAAGCAGGAG ACTCGCTTGA ACTTGGGAGG TGGAGGTTGC      60

AGTGAGCCAA GATTGCACCA ATATACTCCA GCCTGGGTGA CAGAATGAGA CTCTGTCTCA     120

AGAAAAAAAG AAAACAAAAA TCTTCTCCAT TCAAAATGG TTTAGAATTG TATGAGGTGC      180

CAGGGGTCCC AGTTTTATGT ATCATATTAG TTGTAACTTA TGAGCAGCTG TGACAAGCTA    240

CTTGGTTTTC TCCTCAG                                                     257

(2) INFORMATION FOR SEQ ID NO:4:

(i) SEQUENCE CHARACTERISTICS:
        (A) LENGTH: 164 base pairs
        (B) TYPE: nucleic acid
        (C) STRANDEDNESS: single
        (D) TOPOLOGY: linear (xi) SEQUENCE DESCRIPTION: SEQ ID NO:4:

GGGTCTCTCT TTTTGGCATG TCGGCCCTGT TACTCCCTGG GAACTTTGAG TCTTATTTGG      60

AACTTGTGAA GTCCCTGTGT CTGGGGCCAG CACTGATCCA CACAGCTAAG TTTGCACTTG     120

TCTTCCCTCT CATGTATCAT ACCTGGAATG GGATCCGACA CTTG                       164

(2) INFORMATION FOR SEQ ID NO:5:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (xi) SEQUENCE DESCRIPTION: SEQ ID NO:5:

GTAAGTTAAT TCGGGATTTG CACATTTTCT CTGTGAAGGG AGTGGGGAGA CTGGGAGGAT      60

TCTTTCCTTC ATTACTGGGT TTAGTGCTGT TCTTTTTTTT TTTTCCCAAG AGTGGAGTGT     120

CTCGCTCTAT TGCCCAGGCT GGAGTGCAGT GGTGCGATCT CAGCTCACTG CAA             173

(2) INFORMATION FOR SEQ ID NO:6:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (xi) SEQUENCE DESCRIPTION: SEQ ID NO:6:

AATTAACCCT CACTAAAGGG AGTCGACTCG ATCCCAAGTA GTCTGTCTCC CATCATAAAC      60

TTGAACATGA GTTTAAATCT TCTCCTTTTC AAGGCCGGGT GCAGTGGCTC ACACCTGTAA    120

TCTCAGCACT TTGGGAGGCA AAGGTGGGCA GATCACTTGA GGTCAGGAGT TCGAGACCAG    180

CCTGGCCAAC TTGGTGAAAC CCTGTCTCTA CTAAAAATAC AAAAATTAGC TGGGCGTTGT    240
```

```
GGTGGGCACC TGTCATCCCC ACTACTCAGG AGGCTGAAGC AGGAGACTCG CTTGAAACTT      300

GGGAAGTGGA AGTTGCAGTG AACCCAA                                         327
```

(2) INFORMATION FOR SEQ ID NO:7:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (xi) SEQUENCE DESCRIPTION: SEQ ID NO:7:

```
TTGGCACCCA GTTTCTATTA AAGTTGGCCC AATTCTGTCC AACATCTCAA AACAGAAATG       60

CAATATAATG TGTAGATAAG AAAAGGTAAT CTATTTGAGT CCTGTCAGAA GCACTACTCT      120

GGGTCAACAG GAACGGAAGA ATGAAAGCAG CAACAATGGT TATCTAGCTC ATAACTGAAT      180

CCCCAGTGTC TACAACAGTA CCTGACACAT AAATAGGTAC CAATTAATAT TTATGTCATA      240

AACATGCATT CTATGCCTTC AGGGATCTCT TTTAAATATC CCTCTTAAAA ATGAAGAGTT      300

CAGCAGGGCA CAGTGGCTCA CGTCTGTAAT CCTAGCACTT TGGGAAGCTG AAAAGGGTGG      360

ATCACAAGGT CAGATTTGAA AAA                                             383
```

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

```
TGGTGAAACC CTGTCTCTAC                                                  20
```

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

```
TCTATGCCTT CAGGGATCTC                                                  20
```

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

```
ACTTGTGAAG TCCCTGTGTC                                                  20
```

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

-continued

```
AAGTGTCGGA TCCCATTCCA                                                    20

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:12:

GACTCGAGTC GACATCGATT TTTTTTTTTT TTTTT                                   35

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

GCCAGCCCCA TAGAGGACAA CAC                                                23

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:14:

GACTAGTCGA CTGCAGGGGG GGGGGGGGGG                                         30

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:15:

TGCCAGCCCT ACAGAGGACA ACAC                                               24

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:16:

CTGGAGTAAG AACACTACTT TAAACCGTCC                                         30
```

MAMMALIAN ARTIFICIAL CHROMOSOMES AND METHODS OF USING SAME

This application is a divisional of U.S. Ser. No. 08/741,406, filed Oct. 29, 1996 U.S. Pat. No. 5,721,118; which claims the benefit of priority of U.S. Provisional application Ser. No. 60/039,256, filed Oct. 31, 1995, which was converted from U.S. Ser. No. 08/550,717, now abandoned, the entire contents of each of which is incorporated herein by reference.

This invention was made with government support under GM 23241 and GM 18835 awarded by the United States Public Health Service. The government has certain rights in this invention.

BACKGROUND OF THE INVENTION

1. Field of the Invention

The present invention relates generally to molecular biology and molecular genetics and more specifically to mammalian artificial chromosomes.

2. Background Information

The ability to clone and express nucleic acid molecules has resulted in the identification of numerous genes and gene products. As a result of the identification of various genes, molecular differences between normal and diseased conditions are beginning to be recognized. For example, in various disease conditions such as Duchenne muscular dystrophy (DMD), cystic fibrosis and some forms of cancer, mutations in particular genes appear to be the basis for the underlying pathology. In DMD, for example, a mutation in the dystrophin gene can result in the formation of only part of the dystrophin protein, which functions abnormally and contributes to the characteristic signs and symptoms of DMD.

The identification of a molecular defect as the cause of a particular disease suggests possible approaches for ameliorating the disease at the molecular level. Gene therapy, in particular, holds the promise of correcting a pathology such as DMD by introducing a normal dystrophin gene into the muscle cells of an individual suffering from DMD. Unfortunately, the specific molecular defect has been identified in only a handful of diseases. In addition, some genes such as the dystrophin gene contain over one million base pairs and, therefore, are too large to be conveniently transferred from one cell into another using currently available technology.

It has been proposed that the identification of every gene in the human genome will provide insight into the mechanisms responsible for many diseases. Thus, the Human Genome Project was initiated to develop a linkage map for each of the twenty-three pairs of human chromosomes and, ultimately, to obtain the nucleic acid sequence of the entire human genome. However, a structural description, alone, of the human genome is not likely to be sufficient to allow, for example, an understanding of the mechanisms of gene regulation, which can depend on DNA regulatory elements that are located thousands of base pairs or more from the regulated genes.

Currently available mammalian vectors such as retroviral vectors can harbor, at best, DNA fragments containing up to about ten thousand nucleotides. In comparison, yeast vectors such as yeast artificial chromosomes (YACs) can harbor DNA fragments having a few hundred thousand nucleotides. However, such YAC vectors are not stable in mammalian cells and, therefore, cannot be used, for example, as vectors for gene therapy, which, ideally, would be stably maintained in a cell from generation to generation and would express a predictable amount of a gene product. Thus, a need exists for vectors that can contain large fragments of DNA and that are stably maintained in mammalian cells. The present invention satisfies this need and provides related advantages as well.

SUMMARY OF THE INVENTION

The present invention provides a mammalian artificial chromosome (MAC), comprising a centromere and unique cloning site, said MAC containing less than about one-tenth of one percent (0.1%) of the DNA present in a normal haploid mammalian genome from which the centromere was obtained. The invention further provides a MAC, wherein the unique cloning site is a nucleic acid sequence encoding a selectable marker. For example, the invention provides a MAC having a centromere from human chromosome 1 and a nucleic acid molecule encoding a subunit (designated CII-3) of complex II of the mitochondrial electron transport chain, wherein the MAC contains less than about 0.05% of the DNA normally present in a haploid human genome.

The invention also provides methods of using a MAC. For example, the invention provides methods of stably expressing an exogenous nucleic acid molecule in a cell, comprising introducing a MAC containing the exogenous nucleic acid molecule into the cell. The invention also provides a cell containing a MAC expressing an exogenous nucleic acid sequence and a transgenic mammal expressing a selectable marker.

BRIEF DESCRIPTION OF THE DRAWINGS

FIGS. 1A–1E illustrate targeting vectors for introducing a loxP site, which is a target sequence recognized by the bacteriophage P1 Cre recombinase, into MAC-8.2.3.

FIG. 1A shows a targeting vector containing two loxP sites ("loxP site") flanking the neomycin resistance gene ("neo$^R$ gene"), which contains the ATG start codon and the neo gene promoter (located between the 5' loxP site and the ATG sequence). Flanking the loxP sites are genomic DNA sequences of the human CII-3 gene; the darkly stippled bar indicates the CII-3 promoter and the hatched bars indicate CII-3 gene exon or intron sequences. Outside of the CII-3 gene sequences is the HSV-tk gene, which is lost following homologous recombination of the vector into the CII-3 gene present on MAC-8.2.3 (see FIG. 1A).

FIG. 1B shows the targeting vector of FIG. 1A following homologous recombination into the CII-3 gene present on MAC-8.2.3.

FIG. 1C shows the integration site as illustrated in FIG. 1B following excision of the neo gene by the Cre recombinase. Following Cre recombinase action, a single loxP site remains in MAC-8.2.3.

FIG. 1D illustrates a second targeting vector, which can insert into a loxP site such as that shown in FIG. 1C. The circularized vector contains a single loxP site, which can insert into a loxP site present in a MAC due to Cre recombinase activity. The vector contains an exogenous nucleic acid sequence ("cDNA") and the promoterless open reading frame encoding the neo gene product ("neo$^R$(ORF)"). Following insertion of the vector into a loxP site such as that shown in FIG. 1C, a dicistronic transcript (cDNA-neo) is produced; expression of the transcript is from the CII-3 promoter present in MAC-8.2.3 (see FIG. 1E). The construct also contains an internal ribosome entry site ("IRES"), which allows translation of the neo open reading frame in the dicistronic transcript, and a polyadenylation site ("poly (A)"), which allows polyadenylation of the dicistronic transcript.

FIG. 1E shows the vector of FIG. 1D after insertion into the loxP site of FIG. 1C. The CII-3 promoter is shown ("SDH-3 promoter"). Initiator methionine codons ("ATG") and STOP codons ("TAG") also are shown.

DETAILED DESCRIPTION OF THE INVENTION

Figure 1D:
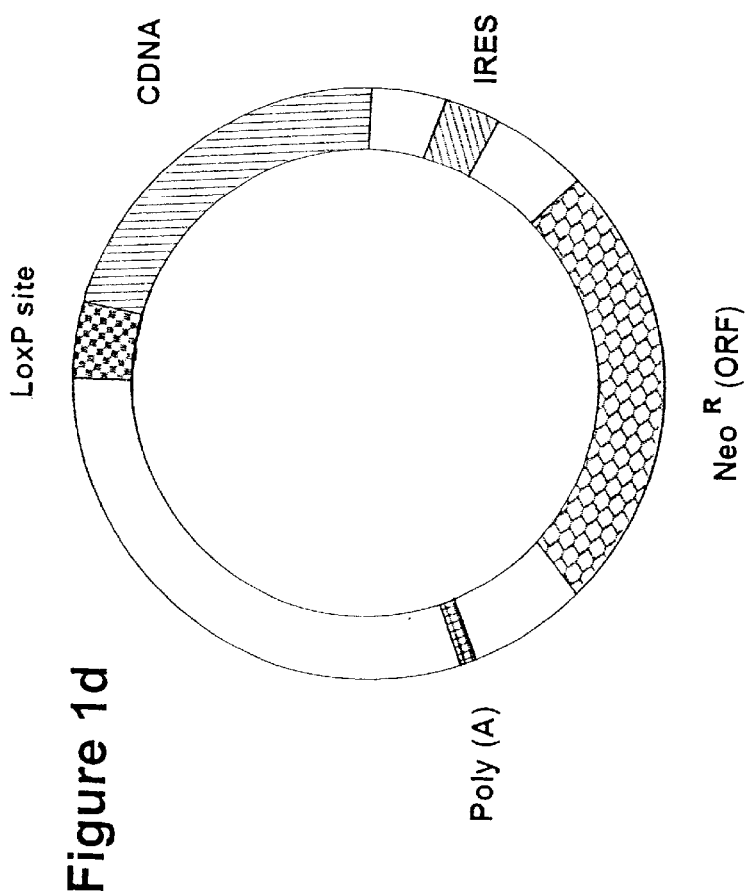

The present invention provides a mammalian artificial chromosome (MAC), comprising a centromere and a unique cloning site, said MAC containing less than 0.1% of the DNA present in a haploid mammalian genome normally containing the centromere. The invention further provides a MAC, wherein the unique cloning site is a nucleic acid sequence encoding a selectable marker. The invention provides, for example, a MAC containing a portion of human chromosome 1, including the human chromosome 1 centromere and the CII-3 gene, which encodes a subunit (CII-3) of complex II of the mitochondrial electron transport chain and allows survival of SDH defective hamster cells in glucose-free medium (Mascarello et al., *Cytogenet. Cell Genet.* 28:121–135 (1980), and Carine et al., *Somat. Cell Genet.* 12:479–492 (1986), each which is incorporated herein by reference). The CII-3 gene encodes one subunit of the complex known as complex II of the mitochondrial electron transport chain. As disclosed herein, a mutation in the CII-3 gene results in deficient succinate dehydrogenase (SDH) activity in a hamster cell line. Thus, reference is made herein to "SDH deficient cells" or "respiration deficient cells" and the like with the understanding that the deficiency is due to a defect of the CII-3 subunit of complex II.

As used herein, the term "mammalian artificial chromosome" or "MAC" means a nucleic acid molecule that 1) forms a centromere, 2) contains an origin of DNA replication, and 3) has a unique cloning site, wherein the size of the MAC, excluding the centromere, is less than about 0.1% of the size of a haploid mammalian genome normally containing the centromere present in the MAC. In particular, a MAC of the invention contains a nucleic acid sequence encoding a selectable marker, which can be used as a site into which an exogenous nucleic acid sequence can be cloned. Due, in part, to the structural characteristics described above, a MAC is characterized further in that it is stably and autonomously maintained in a host cell and, therefore, is present in both daughter host cells following mitosis of the parental host cell. A MAC can be prepared from any mammalian chromosome, including a human, murine, bovine, ovine, porcine or other mammalian chromosome such as human chromosome 1 as exemplified herein.

A Chinese hamster cell line, XEW8.2.3, which is a host cell for a MAC having a human chromosome 1 centromere and the human CII-3 gene and containing less than about 0.05% of the DNA in a normal haploid human genome, has been deposited in accordance with the requirements of the Budapest Treaty with the American Type Culture Collection (ATCC) on Oct. 31, 1995, as ATCC Accession No: ATCC CRL 11992. For convenience, the MAC present in the cell line available as ATCC Accession No: ATCC CRL 11992 is referred to herein as MAC-8.2.3.

A MAC of the invention is defined, in part, by having a size, excluding the centromere, that is less than about 0.1% of DNA present in a normal mammalian haploid genome, the particular mammalian genome being that genome from which the centromere is obtained. For example, MAC-8.2.3 is defined in terms of a human genome because the centromere of MAC-8.2.3 was obtained from human chromosome 1. A human haploid genome contains about $3.3 \times 10^9$ base pairs of DNA. Thus, a MAC having a centromere obtained from a human genome contains a centromere and less than about 3.3 million base pairs. MAC-8.2.3, for example, contains a centromere and, in addition, about 1–2 million base pairs of DNA on the arms flanking the centromere. It is recognized, however, that, while a MAC is defined as having a size that is less than about 0.1% of a normal mammalian haploid genome, the MAC can be used as a vector and, therefore, can contain inserted DNA sequences that can be several million base pairs in size. Methods for estimating the size of a putative MAC are known in the art (see, for example, Carine et al., supra, 1986).

As used herein, the term "less than 0.1% of the DNA present in a haploid mammalian genome normally containing the centromere" refers to the amount of DNA that contains repetitive DNA sequences known as Alu sequences. In general, Alu-containing DNA is considered to be present in the chromosomal arm, but not in the centromeres. Thus, a MAC as defined herein, contains, in addition to a centromere, less than about $3.3 \times 10^6$ base pairs of DNA on the arms flanking the centromere. The amount of DNA in a MAC that contains Alu sequences can be estimated using methods well known in the art (see, for example, Carine et al., supra, 1986).

As used herein, the term "centromere" means the DNA sequence that normally is present at the junction between the two arms of a chromosome and is associated with the structure to which the spindle fibers attach during mitosis. For purposes of the present invention, a centromere is identified by its function of providing stable segregation during cell division of a nucleic acid sequence linked to the centromere. While it is recognized that the spindle fibers likely do not attach directly to the DNA sequence contained in a centromere but, instead, attach to a nucleoprotein complex formed, in part, by the DNA sequence, no mechanism is proposed herein as to how a centromere functions. The term "centromeric fragment" is used herein to mean a portion of a chromosome containing a centromere. As disclosed herein, a centromeric fragment can be obtained, for example, by irradiating a cell at a dose that results in breakage of the chromosomes.

The skilled artisan would recognize that a MAC containing an origin of DNA replication can be identified by detecting the MAC in both daughter cells formed following mitosis of the parental host cell. The presence of a selectable marker in a MAC can be identified by determining that a cell containing the MAC has the characteristics conferred by the marker. Selectable markers are described in greater detail below.

As used herein, the term "host cell" is used broadly to mean a cell containing a MAC. XEW8.3.2 is an example of a host cell. In general, a host cell is useful for maintaining a MAC and is a convenient "vessel" for manipulating the MAC. For example, an exogenous nucleic acid molecule can be introduced into a MAC by transfecting the host cell containing the MAC with the nucleic acid sequence under conditions that allow the exogenous sequence to be inserted into the MAC. An exogenous nucleic acid sequence can be inserted into MAC-8.2.3, for example, by homologous recombination of a targeting vector containing the sequence with the CII-3 gene present in MAC-8.2.3.

As used herein, the term "exogenous nucleic acid sequence" when used in reference to a MAC means a nucleotide sequence that is not normally present on the MAC. In contrast, the term "endogenous nucleic acid sequence" means a nucleotide sequence normally present on the MAC. Thus, the human CII-3 gene, which is normally present in a pericentric location on human chromosome 1, is an example of an endogenous nucleic acid sequence with reference to MAC-8.2.3 (see, for example, SEQ ID NOS: 3–7). Any other nucleic acid sequence that, for example, is inserted into the CII-3 gene sequence on MAC-8.2.3 is considered an exogenous nucleic acid sequence.

An exogenous nucleic acid sequence can be a fragment of genomic DNA, which can be prepared from intact genomic DNA by physical disruption using, for example, irradiation or sonication or by chemical cleavage using, for example, a restriction endonuclease such as a rare cutting endonuclease that cleaves genomic DNA at relatively few sites. A population of MACs containing diverse fragments of genomic DNA prepared from a particular cell type can constitute a genomic library, which can be screened, for example, to identify fragments containing particular genes of interest. Since a MAC can contain a fragment of genomic DNA having several million base pairs, such a genomic library can contain, for example, a complex genetic locus, thereby providing a model system useful for identifying the regulatory regions such as enhancers or silencers that are involved in regulation of gene expression from the locus and the regulatory factors that bind to such regions. Thus, a MAC is useful as a cloning vector and provides the additional advantage that very large fragments of DNA on the order of several million bases can be cloned into and maintained in the MAC.

An exogenous nucleic acid sequence also can be inserted into a MAC for the purpose of being expressed. Such an exogenous nucleic acid sequence can be, for example, a particular gene such as the gene encoding dystrophin; or can be a cDNA, which encodes a gene product; or can be a sequence that, when expressed, is complementary to a nucleic acid of interest and acts, for example, as an antisense molecule, which can hybridize to a particular DNA or RNA sequence, or acts as a ribozyme, which can hybridize to and cleave a particular RNA. Thus, a MAC also can be useful as an expression vector and provides the additional advantage that it is stable through numerous rounds of cell division.

An exogenous nucleic acid sequence also can include a regulatory element involved in the regulation of gene expression or of translation of a transcript. Such regulatory elements such as a promoter, enhancer, silencer, polyadenylation signal sequence, ribosome entry site, signal peptide encoding sequence, nuclear localization signal encoding sequence and the like are well known in the art and can be inserted into a MAC, as desired, using well known methods of recombinant DNA technology (see, for example, Kriegler, *Gene Transfer and Expression: A laboratory manual* (W.H. Freeman and Co., New York; 1990), which is incorporated herein by reference).

Various types of regulatory elements are available and are selected based on the particular purpose for which a MAC is being constructed. A promoter element, for example, can be constitutive such as the cytomegalovirus promoter or Rous sarcoma virus promoter, or can be inducible such as the metallothionein promotor. In addition, a promoter can be a tissue specific promotor such as the myoD promoter, which is expressed only in muscle cells, or the lck promoter, which is expressed only in T cells, or can be a promoter that is active only during a particular stage of development. Similarly, enhancers can be constitutive or inducible or, like the SV40 enhancer, can be constitutively active and, in addition, can be induced to a higher level of activity. Such gene regulatory elements and translation regulatory elements generally are relatively small and can be synthesized using routine methods of DNA synthesis or can be purchased in vectors from commercial sources.

A MAC is characterized, in part, by containing a unique cloning site. As used herein, the term "unique cloning site" means a nucleic acid sequence that can be targeted for insertion of an exogenous nucleic acid sequence. As disclosed herein, a unique cloning site can be, for example, a specific target site such as the loxP sequence, which is a target for the Cre recombinase, or an FLP site, which is a target for the FRP recombinase (see below). The presence of such a cloning site in a MAC allows the site specific integration of an exogenous nucleic acid sequence into the MAC.

A unique cloning site also can be a nucleic acid sequence encoding a gene product, provided the nucleic acid sequence is present in a single copy on the MAC. As disclosed herein, the human CII-3 gene present on MAC8.2.3 is an example of an endogenous, single copy gene useful as a cloning site. If desired, an exogenous nucleic acid sequence can be cloned into such a single copy nucleic acid sequence present on the MAC using, for example, methods of homologous recombination as disclosed herein. For example, where an exogenous nucleic acid sequence is cloned into the CII-3 gene present on MAC8.2.3, the exogenous nucleic acid sequence is linked to targeting sequences comprising a portion of the CII-3 gene.

As used herein, the term "portion of a nucleic acid sequence of a human CII-3 gene" means a nucleotide sequence of the human CII-3 gene that is of a sufficient length to allow specific hybridization of the sequence to an endogenous human CII-3 gene. Specific hybridization can be identified by performing routine hybridization reactions with a selected nucleotide sequence of the CII-3 under stringent hybridization conditions. Generally, such a nucleotide sequence is at least about 14 nucleotides in length. In addition, since specificity increases with increasing length of a sequence, a nucleotide sequence that is at least about 18 nucleotides in length can be particularly useful as a targeting sequence. Furthermore, it is well known that the efficiency of homologous recombination increases with the length of the targeting sequence. Thus, targeting sequences of at least about 100 nucleotides and up to several kilobases can provide relatively high efficiency of insertion of an exogenous nucleic acid sequence into a articular locus. Such targeting sequences can be selected, for example, from the genomic CII-3 sequences disclosed herein as SEQ ID NOS: 3, 5, 6 or 7. Such a sequence also can be selected from SEQ ID NO: 4, which is an exon of the CII-3 gene, or can be selected from nucleotide sequences of the CII-3 cDNA (SEQ ID NO: 1). Using methods as disclosed in Example II, additional sequences of the human CII-3 gene can be obtained, thereby providing substantially longer targeting sequences useful in the invention.

It should be recognized that when a targeting sequence is selected from a coding region of a gene such as the human CII-3 gene, such a sequence generally must be longer than a sequence selected from a noncoding region of the gene. With regard to the human CII-3 gene present on MAC8.2.3, for example, the presence of related human CII-3 genes or pseudogenes (see Example II) and the high degree of sequence identity shared between CII-3 coding sequences of different species can result in insertion of the targeting vector into genomic DNA sequences other than the human CII-3 gene present on MAC8.2.3. Such nonspecific insertion of a targeting vector can be minimized, for example, by including noncoding sequences such as intron sequences in a targeting sequence comprising a coding sequence. However, even if insertion of a targeting vector occurs in a gene other than the human CII-3 gene present on MAC8.2.3, such nonspecific insertions can be identified using methods as disclosed herein or otherwise known in the art. For example, nonspecific insertion can be identified by a change, or lack thereof, in the ability of host cells containing the MAC to survive under selective conditions. In addition, nonspecific insertion can be identified, for example, by fluorescence in situ hybridization.

In particular, a unique cloning site can be a nucleic acid molecule encoding a selectable marker, which can be an exogenous or endogenous nucleic acid sequence. As used herein, the term "selectable marker" means a nucleic acid sequence or a protein or peptide expressed therefrom that confers upon a cell containing the marker the characteristic that the cell can be identified among a population of cells that do not contain the marker. Thus, a cell containing a MAC expressing a selectable marker displays a phenotype that the cell did not display prior to expression of the selectable marker. A selectable marker can be a positive marker, which allows direct identification of a cell containing the marker, or can be negative marker, which kills a cell, thereby allowing identification of the cell indirectly by its absence. For convenience, reference is made herein to a MAC containing a selectable marker, since a MAC containing such a unique cloning site is exemplified. It should be recognized, however, that a MAC of the invention is characterized, in part, by containing a unique cloning site and that a selectable marker is one embodiment of a unique cloning site.

A selectable marker can confer upon a cell expressing the marker the ability to survive in an environment that otherwise kills cells not expressing the marker. The CII-3 gene is an example of such a selectable marker, which also is an endogenous nucleic acid sequence in MAC-8.2.3. The CII-3 gene is an example of a selectable marker that corrects a genetic defect in a mutant cell, such that the cell attains a wild type phenotype. The use of such a selectable marker requires that a mutant cell type is available, such that a mutant cell containing a MAC can be identified by expression of the marker. A diseased cell such as a muscle cell expressing a mutant dystrophin gene in a muscular dystrophy patient is another example of a mutant cell. Thus, a normal dystrophin gene can be a selectable marker, which, when introduced using a MAC into the mutant muscle cell, results in the previously mutant muscle cells attaining a normal muscle cell phenotype.

A selectable marker can allow a cell to survive in the presence of a drug that otherwise would kill the cell. Such selectable markers, include, for example, positive selectable markers that confer resistance to neomycin (geneticin; G418), puromycin or hygromycin B. In comparison, a selectable marker such as the *Herpes simplex* virus thymidine kinase (HSV-tk) is useful for either positive selection, for example, in a cell that is deficient in thymidine kinase activity, or negative selection, whereby cells expressing HSV-tk are killed by exposure to gancyclovir. Such selectable markers are useful because they confer an identifiable phenotype on an otherwise normal cell and, therefore, do not require the availability of a mutant cell. These and other selectable markers are well known in the art and commercially available (see, for example, Sambrook et al., *Molecular Cloning: A laboratory manual* (Cold Spring Harbor Laboratory Press 1989), which is incorporated herein by reference; see pages 16.9–16.15).

In addition, a selectable marker can be a product that allows a cell containing the MAC to be identified visually among a population of cells, some of which do not contain the selectable marker. Examples of such selectable markers include the green fluorescent protein (GFP), which can be visualized by its fluorescence; the luciferase gene, which, when exposed to its substrate luciferin, can be visualized by its luminescence; and β-galactosidase (β-gal), which, when contacted with its substrate, produces a characteristic color. Such selectable markers are well known in the art and the nucleic acid sequences encoding these markers are commercially available (see Sambrook et al., supra, 1989).

As disclosed herein, a MAC was prepared by isolating and characterizing a portion of a human chromosome containing a selectable marker. Specifically, a portion of human chromosome 1, also called minichromosome 1, containing the human CII-3 gene was selected in Chinese hamster cells that have a mutation in the CII-3 gene. Although the minichromosomes have been partially characterized (Carine et al., supra, 1986; Carine et al., supra, 1989; see, also, Solus et al., *Somat. Cell Mol. Genet.* 381–391 (1988), which is incorporated herein by reference), prior to the present disclosure that the defect in the host Chinese hamster cells is due to a mutation in the CII-3 gene and that the defect is complemented by a normal human CII-3 gene present on the minichromosome 1, the minichromosome was not considered useful as a MAC.

MAC-8.2.3 was selected in mutant Chinese hamster fibroblasts that are defective in succitate dehydrogenase (SDH) activity (Scheffler, *J. Cell. Physiol.* 83:219–230 (1974); Soderberg et al., *Cell* 10:697–702 (1977), each of which is incorporated herein by reference). The SDH-deficient hamster cells, designated CCL16-B9, are the host cells that contain MAC-8.2.3 and are deposited as ATCC Accession No. ATCC CRL 11992 (CCL16-B9 cells containing MAC-8.2.3 also are known as XEW8.2.3 cells). As a result of the SDH deficiency, CCL16-B9 cells require glucose in the growth medium and cannot grow in medium in which galactose is substituted for glucose.

Succinate dehydrogenase is part of complex II of the mitochondrial electron transport chain, linking the reactions of the tricarboxylic acid cycle to oxidative phosphorylation. This complex consists of four polypeptide subunits: a 70 kiloDalton (kDa) flavoprotein (FP), a 27 kDa iron-containing protein (IP), and two small integral membrane anchor proteins (CII-3 and CII-4; 15 and 7–9 kDa, respectively). Each subunit is encoded by a nuclear gene (SDH-1, SDH-2, SDH-3 and SDH-4, respectively) in eukaryotic cells. While an FP-IP complex, alone, can be dissociated from the inner mitochondrial membrane by chaotropic ions and assayed for succinate dehydrogenase activity using artificial electron acceptors, studies with yeast mutants indicate that the membrane anchor proteins are essential for the assembly of a functional complex II and SDH activity.

In order to identify the genetic defect in the CCL16-B9 hamster cells, somatic cell fusions were made between the mutant hamster cells and human cells and two independent primary (human×hamster) hybrids, XJM12.1.2 and XJM12.1.3, that grew in galactose-containing medium were obtained (Mascarello et al., supra, 1980). Secondary hybrids then were selected by fusing heavily irradiated XJM12.1.3 cells with the original mutant Chinese hamster CCL16-B9 cells and again selecting for cells that grew in galactose-containing medium (respiration competent hybrids; see Carine et al., supra, 1986).

Examination of the primary and secondary hybrid cell lines revealed the presence of a single human minichromosome consisting of a centromeric fragment of human chromosome 1 (Carine et al., supra, 1986; Carine et al., supra, 1989). Hybrid cells retaining an apparently intact human chromosome 1 also were examined. Spontaneous loss of the intact chromosome 1 resulted in loss of SDH activity and reversion to the respiration deficient condition; spontaneous segregation of the human minichromosome 1 has not been observed over many years in culture.

The minichromosomes first were observed in metaphase spreads in the light microscope after in situ hybridization with human Alu sequences. The minichromosome present in XEW8.2.3 also was examined by electron microscopy and was similar in length to the kinetochores. Based on the assumption that Alu sequences are uniformly distributed in the human genome, except in centromeres, telomeres and a few other regions containing tandem repeats, the minichromosome in 8.2.3 was estimated to contain about 1–2 million base pairs of human DNA, which is about 0.05% of the DNA contained in a normal haploid human genome (see Carine et al., supra, 1986; Carine et al., supra, 1989; see, also, Solus et al., supra, 1988).

All of the minichromosomes examined contained a small fraction of the pericentric chromatin from the long arm of human chromosome 1, as characterized by a satellite III DNA sequence present exclusively at 1q12. The minichromosomes also contained α-satellite DNA sequences, which are characteristic of human centromeres. Members of one such family were cloned from a genomic library prepared from the hybrid XJM12.1.3 and found to consist of a 340 bp Eco RI repeat containing two degenerate 170 bp monomers characteristic of alphoid DNA. In addition, another chromosome 1-specific α-satellite sequence, a 1.9 kb Hind III repeat, was present on the minichromosomes (Carine et al., supra, 1989).

A double labeling in situ hybridization experiment was performed using α-satellite and satellite III probes and visualized by electron microscopy. The results confirmed that the XEW8.2.3 minichromosome contains α-satellite sequences; satellite III DNA sequences were barely detectable. These results indicate that breakpoints occurred on either side of the centromere, retaining a small fraction of the pericentric heterochromatin on one side and about 1–2 million base pairs of the short arm of chromosome 1.

An anonymous single copy sequence was cloned from the minichromosome present in the XJM12.1.3 primary hybrid cell line. The single copy sequence also was present on the minichromosome present in the XJM12.2.2 primary hybrid cell line, as well as on the intact human chromosome 1. In comparison, the minichromosome present in the XEW8.2.3 secondary hybrid cell line, which was derived from XJM12.1.3, does not contain the anonymous sequence (Solus et al., supra, 1988), indicating that the anonymous sequence was located distal to the selectable CII-3 gene relative to the centromere (Carine et al., supra, 1989; Waye et al., Genomics 1:43–51 (1987); Willard, supra, 1987).

Indirect studies suggested that the mutant hamster cells had a defect in the gene for the IP subunit of SDH (Soderberg et al., supra, 1977). However, isolation and mapping of the genomic DNA, including the promoter, of the IP gene revealed that the IP gene was located at the distal end of the short arm of chromosome 1 (1p36.1–2) and was not present on the minichromosomes (Leckschat et al., Somat. Cell Mol. Genet. 19:505–511 (1993), which is incorporated herein by reference). Furthermore, an IP cDNA did not complement the respiration deficient condition when transfected into the mutant CCL16-B9 hamster cells. Thus, despite substantial characterization of the minichromosomes, a gene that complemented the SDH deficiency in the mutant hamster cells was not identified.

A bovine CII-3 cDNA (see Au et al., Gene 149:261–265 (1994), which is incorporated herein by reference) complements the SDH deficient phenotype in the mutant CCL16-B9 cells. In addition, a hamster CII-3 cDNA was isolated, the DNA sequence was determined and the encoded amino acid sequence was deduced. At the amino acid level there is about 82% identity between the wild type hamster and bovine CII-3 proteins. In comparison, the CII-3 cDNA isolated from mutant CCL16-B9 cells contains a single base mutation in the coding sequence for the CII-3 protein that produces a premature STOP codon and results in the truncation of 33 amino acids from the C-terminus and the SDH deficient phenotype in CCL16-B9 cells (see Example I). Furthermore, the gene encoding the human CII-3 subunit of complex II of the mitochondrial electron transport chain was mapped on human chromosome 1 and on the minichromosome, indicating that the human CII-3 gene is present within about 1–2 million base pairs of the centromere. These results indicated that MAC-8.2.3, which is present in the (human×hamster) secondary hybrid XEW8.2.3. cells, contains a normal copy of the human CII-3 gene that complements the mutation in the CCL16-B9 hamster cells.

As disclosed herein, a human CII-3 cDNA (SEQ ID NO: 1) has been cloned and expression of the human CII-3 cDNA also complements the mutation in the SDH-deficient B9 hamster cells. Furthermore, human genomic CII-3 DNA sequences were isolated (see FIG. 2; SEQ ID NOS: 3–7) and the human CII-3 gene was localized to MAC8.2.3, which is derived from human chromosome 1. The identification of this locus in MAC-8.2.3 provides a unique cloning site for inserting an exogenous nucleic acid sequence into MAC8.2.3.

Since MAC-8.2.3 contains a functional human CII-3 gene, a respiration-deficient hamster cell containing MAC-8.2.3 was identified by selecting cells that grew in galactose-containing medium. Thus, the CII-3 gene provides a selectable marker useful for identifying a CCL16-B9 hamster cell containing MAC-8.2.3. Significantly, identification of the CII-3 gene on MAC-8.2.3 provides a unique locus useful for site specific insertion of an exogenous nucleic acid sequence, thus making MAC-8.2.3 useful as a vector.

A MAC of the invention is useful as a vector for delivering an exogenous nucleic acid sequence into a cell and provides significant advantages over previously known vectors. For example, a MAC can contain an exogenous nucleic acid sequence having several thousand base pairs (kbp) up to several million base pairs. Thus, a MAC can contain an entire gene such as the 2300 kbp dystrophin gene, which is mutated in muscular dystrophy patients. In addition, a MAC is stably maintained as a single entity in a cell. Thus, a MAC provides the additional advantage that a gene contained in and expressed from a MAC produces a unit dosage of an encoded gene product. Furthermore, a MAC is replicated along with the normal complement of chromosomes in a cell and, therefore, is passed to all of the daughter cells following a mitotic or meiotic division. Also, a MAC does not integrate into the genomic DNA in a cell but is maintained as an autonomous entity. Accordingly, introduction of an exogenous nucleic acid molecule contained in a MAC into a cell obviates any concern that the exogenous nucleic acid molecule may integrate into and disrupt the function of a normal gene in the cell.

The identification of the unique CII-3 gene sequence on MAC-8.2.3 provides a target site, into which an exogenous nucleic acid sequence can be inserted. A MAC containing an exogenous nucleic acid sequence can be transferred into a mammalian cell such as a mammalian stem cell, where the exogenous nucleic acid sequence can be expressed, if desired. Methods for introducing an exogenous nucleic acid sequence into a defined nucleic acid sequence such as one or more of the sequences shown as SEQ ID NOS: 3–7 are disclosed herein or otherwise known in the art. For example, an exogenous nucleic acid sequence can be targeted into the CII-3 gene using homologous recombination methods as have been used to produce gene knock-outs in embryonic stem cells in mice (see, for example, Gossen and Vijg, Trends Genet. 9:27–31 (1993); Frohman and Martin, Cell 56:145–147 (1989); Capecchi, Science 244:1288–1292 (1989); Westphal and Gruss, Ann. Rev. Cell Biol. 5:181–196 (1989); Zijlstra et al., Nature 342:435–438 (1989), each of which is incorporated herein by reference). In particular, the human CII-3 genomic DNA sequences shown as SEQ ID NOS: 3, 5, 6 or 7 can be useful in a targeting vector for homologous recombination because these sequences do not contain coding sequences or regulatory sequences and, therefore, are expected to occur as unique sequences in a cell that does not otherwise contain a human chromosome 1. A dominant selectable marker conferring, for example, neomycin resistance or puromycin resistance also can be introduced into MAC-8.2.3, thus facilitating selection and identification of virtually any mammalian cell containing the MAC (see, for example, Ayares et al., Proc. Natl. Acad. Sci., USA 83:5199–5203 (1986), which is incorporated herein by reference).

Figure 1E:
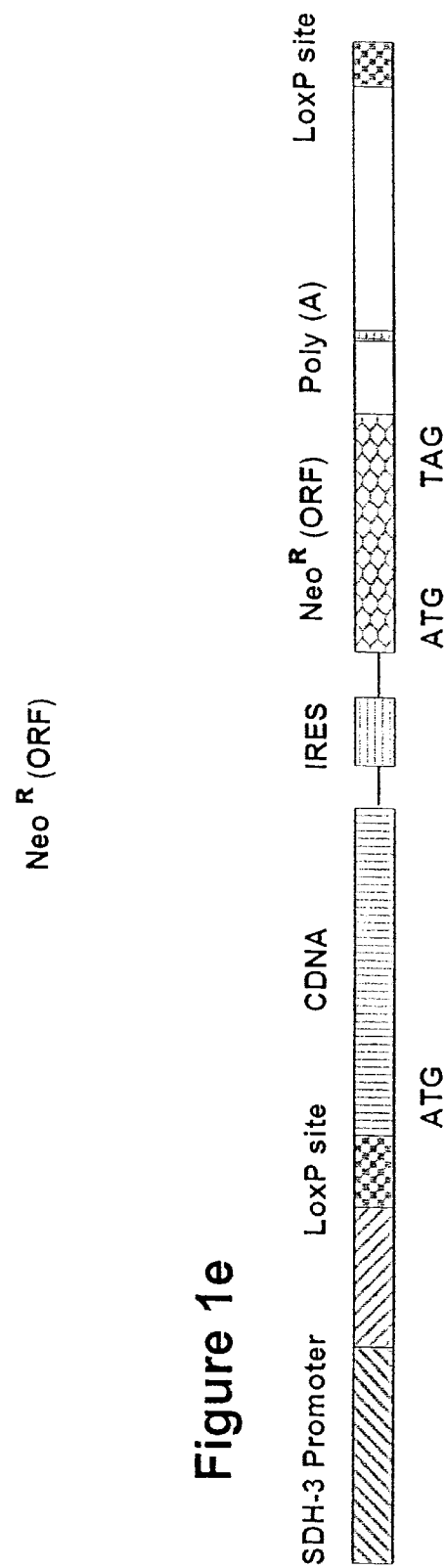

A characteristic of a MAC that makes it particularly useful a vector is that an exogenous nucleic acid sequence can be inserted into a unique cloning site present in the MAC in a site specific manner. A particularly useful method of introducing an exogenous nucleic acid sequence into a MAC in a site specific manner utilizes a recombinase and recombinase recognition site, wherein the recombinase recognition site provides a unique cloning site. For example, site specific integration using the Cre recombinase and loxP recombinase recognition site from phage P1 (see Sauer, Meth. Enzymol. 225:890–900 (1993), which is incorporated herein by reference) or the yeast FLP/FRT system (see O'Gorman et al., Science 251:1351–1355 (1991), which is incorporated herein by reference) provides a convenient and efficient means for introducing an exogenous nucleic acid sequence into a MAC such as MAC-8.2.3 (see Example III and FIG. 1). Use of a site specific recombinase system for introducing a nucleic acid into a MAC provides the advantage that integration of the exogenous sequence does not disrupt or otherwise inactivate a characteristic of the MAC such as the ability to replicate or to segregate properly during cell division.

The FLP site specific recombinase has been characterized from Saccharomyces cerevisiae (Broach and Hicks, Cell 21:501–508 (1980), which is incorporated herein by reference) and the FLP recombination target (FRT) site has been identified (Jayaram, Proc. Natl. Acad. Sci., USA 82:5875–5879 (1985); Senecoff et al., Proc. Natl. Acad. Sci., USA 82:7270–7274 (1985), each of which is incorporated herein by reference). Functionality of the FRT/FLP system has been demonstrated in mammalian cells (O'Gorman et al., supra, 1991). In one experiment, a β-galactosidase (β-gal) gene sequence was disrupted by inserting a nucleic acid sequence flanked by two FRT sites; the insertion prevented expression of the β-gal gene product. Cotransfection into various mammalian cell lines of the disrupted β-gal gene and an FLP expression vector resulted in precise excision of the insert by the recombinase, leaving behind one FRT site, which preserved the β-gal reading frame, and restoring β-gal activity. In a second experiment, a single FRT site was inserted into a chromosome, then the cells were cotransfected with a vector containing a second FRT site and the FLP expression vector. The vector containing the FRT site was integrated specifically at the chromosome site containing the FRT site.

Site specific DNA recombination in mammalian cells also has been performed using the Cre recombinase of bacteriophage PI and the loxP target site, which consists of 34 base pair repeats (see, for example, Orban et al., Proc. Natl. Acad. Sci., USA 89:6861–6865 (1992); Fukushige and Sauer, Proc. Natl. Acad. Sci. USA 89:7905–7909 (1992); Lakso et al., Proc. Natl. Acad. Sci., USA 89:6232–6236 (1992), each of which is incorporated herein by reference). For example, transgenic mice having a loxP-(β-gal)-loxP transgene positioned at a unique site have been produced (Orban et al., supra, 1992). When mated with transgenic mice carrying a Cre gene under control of the lck promoter, which is active only in thymocytes, doubly transgenic mice expressed the Cre recombinase, resulting in Cre-mediated recombination and excision of the β-gal gene in a cell specific manner. The loxP-Cre system also was used to delete a DNA polymerase b gene segment in T cells and to delete specific segments in the IgH locus (Gu et al., Science 265:103–106 (1994); Gu et al., Cell 73:1155–1164 (1993), each of which is incorporated herein by reference). In addition, purified Cre recombinase was introduced directly into osteosarcoma cells by lipofection and catalyzed site specific integration of a loxP targeting (Baubonis and Sauer, Nucl. Acids Res. 21:2025–2029 (1993), which is incorporated herein by reference).

In addition to its utility as a vector, a MAC such as MAC-8.2.3 can be used to identify the essential elements of a mammalian chromosome, including the nucleic acid sequences required to confer activity as a centromere, a telomere or an origin of DNA replication. Furthermore, large genomic DNA fragments cloned into a MAC provide a system for identifying and characterizing nucleic acid sequences required for coordinate regulation of gene complexes such as the immunoglobulin gene locus. Also, the ability of a MAC to segregate in a completely stable manner during mitosis provides a system for defining the mechanisms and factors involved in this process.

MAC-8.2.3, for example, contains a human chromosome 1 centromere that functions appropriately in Chinese hamster cell line (Carine et al., supra, 1989). Human chromosomes characteristically have large tandem repeats of the alphoid family of satellite repeats at their centromere; individual chromosomes can be distinguished by which member(s) of the alphoid family of repeats is present, based on restriction mapping and high stringency hybridizations (see, for example, Waye and Willard, *Nucl. Acids Res.* 15:7549–7569 (1987); Willard et al., *Trends Genet.* 3:192–198 (1990)). Since the human centromere alphoid sequences do not cross-hybridize with Chinese hamster DNA sequences, the centromere sequences of hamster and human chromosomes are substantially different. Nevertheless, human chromosomes, including MAC-8.2.3, are stably maintained in (human×hamster) hybrid cell lines. The use of MAC-8.2.3 provides a unique system for identifying the mechanisms involved in maintaining chromosome stability in a cell.

An essential feature of centromeric DNA sequences is the ability to become associated with special proteins to form a unique type of chromatin to which the proteins of the kinetochore become attached. Only a few such proteins have been identified. Kinetochores likely consist of a series of repeated structural motifs because more than 10 microtubules attach to each side of a metaphase chromosome. A MAC such as MAC-8.2.3 is useful for identifying the proteins involved in kinetochore formation and spindle fiber attachment. An understanding of the factors involved in spindle fiber attachment to a centromere can provide insight into the mechanism responsible for appropriate chromosome segregation during mitosis. Such an understanding can lead to the development of methods for preventing, for example, improper segregation, which can result in trisomy or in loss of a chromosome in a daughter cell.

The present invention also provides methods for preparing a MAC, comprising fragmenting a parental chromosome and selecting a centromeric fragment of the chromosome containing less than about 0.1% of the DNA present in a normal haploid mammalian genome containing the parental chromosome. The MAC is selected based on the presence of a selectable marker on the centromeric fragment, which further provides a unique cloning site that can be used as a site to insert an exogenous nucleic acid sequence or that can be further modified, for example, to contain a recombinase recognition site.

As used herein, the term "parental chromosome" means the normal cellular chromosome from which the MAC was derived. For example, MAC-8.2.3 was derived from and contains the centromere of human chromosome 1, which, therefore, was the parental chromosome of MAC-8.2.3 (see Example I). A MAC is prepared by obtaining a centromeric fragment of a chromosome containing a selectable marker. If desired, the MAC can be genetically engineered to provide one or more desirable characteristics. In particular, a MAC can be genetically engineered to contain, in addition to the selectable marker, an exogenous nucleic acid sequence such as a gene or a cDNA, which can encode a second selectable marker; an entire genetic locus, including regulatory elements such as enhancers, which can be several kilobases upstream or downstream of a gene; or a randomly produced fragment of genomic DNA.

Yeast artificial chromosomes (YACs) have been developed by assembling essential elements of yeast DNA, including centromeres, telomeres and replication origins (Burke et al., *Science* 236:806–812 (1987); Schlessinger, *Trends Genet.* 6:248–258 (1990)). However, it is not possible to apply the methods used in constructing a YAC similarly to construct a MAC because the essential elements such as mammalian origins of DNA replication and mammalian centromeres are not well characterized (see Huxley et al., *BioTechnology* 12:586–590 (1994); Brown, *Curr. Opin. Genet. Devel.* 2:479–486 (1992); Lewin, *J. NIH Res.* 7:42–46 (1995)).

As disclosed herein, a MAC can be prepared, for example, by telomere associated chromosome truncation or by irradiating a cell at a dose that causes fragmentation of the chromosomes in the cell and selecting therefrom a MAC based on the presence of an endogenous selectable marker located near the centromere (pericentric). Such pericentric endogenous selectable markers include, for example, the CII-3 gene or another gene that can be identified, for example, by searching in the Human Genome Database (GDB; v.6.0) accessible via the Internet, which is incorporated herein by reference.

Since pericentric endogenous selective markers are expected to be rare in mammalian chromosome, a selectable marker generally will be randomly or site specifically inserted into the pericentric region of a chromosome. For example, a selectable marker conferring neomycin resistance can be inserted site specifically by homologous recombination into a gene that is located in a pericentric region of a chromosome. A pericentric gene can be identified in the GDB database (see above). For example, the neo gene can be targeted into the gene encoding the high molecular weight neurofilament peptide, NF-H, which is a pericentric gene located on chromosome 1 at 1p12 (Lieberburg et al., *Proc. Natl. Acad. Sci., USA* 86:2463–2467 (1989), which is incorporated herein by reference), into the gene encoding an Fc Gamma receptor, which has been mapped to 1p12 (Mascarena et al., *Cytoaenet. Cell Genet.* 73:157–163 (1996), which is incorporated herein by reference), or into any other pericentric gene. Following integration of the selectable marker, the chromosomes can be fragmented, for example, by telomere associated truncation, and a MAC can be obtained by somatic cell fusion, followed by selection of neomycin resistant hybrid cells and identification of a selected hybrid cell containing a MAC, as defined herein.

A selectable marker also can be targeted to an endogenous pericentric nucleic acid sequence other than a pericentric gene. For example, a selectable marker can be targeted using homologous recombination to a unique pericentric nucleic acid sequence or to a satellite DNA sequence, which generally is present in the region of the centromere (see Carine et al., supra, 1989). Following integration of the selectable marker into the chromosome, a MAC is obtained, for example, by fragmenting the chromosomes containing the selectable marker, fusing the cells containing the fragmented chromosomes with a second cell line, which can be the same cell type as the first cell line, and selecting hybrid cells that contain a centromeric fragment of a chromosome containing the selectable marker, wherein the centromeric fragment has the characteristics of a MAC. Thus, based on the methods disclosed herein, the skilled artisan can prepare a MAC having characteristics similar to MAC-8.2.3 or a MAC having other characteristics as desired.

The invention also provides methods of stably expressing a selectable marker in a cell, comprising introducing a MAC containing the selectable marker into the cell. For example, the human CII-3 gene product is a selectable marker that is stably expressed in mutant hamster CCL16-B9 cells, which do not express a functional hamster CII-3 gene product.

As used herein, the term "stably expressed" when used in reference to a selectable marker means that the nucleic acid molecule encoding the marker is maintained and expressed in a cell line. In particular, a selectable marker is stably expressed from generation to generation in a cell type that traverses the cell cycle and, ultimately, divides. The ability to stably express a selectable marker in a cell is due to the ability of a MAC to be replicated during the cell cycle and to segregate with a daughter cell during cell division. It is recognized, however, that some cells such as muscle cells generally do not divide. Nevertheless, a selectable marker is considered to be stably expressed in a non-dividing cell if the MAC containing the selectable marker is stably and autonomously maintained in the cell and if the selectable marker is expressed as appropriate. In this regard, it is further recognized that the term "stably" when used in reference to the expression of a selectable marker does not necessarily mean that the marker is "always" or "constantly" expressed because expression of a selectable marker is regulated, in part, by the particular gene regulatory elements linked to the marker. For example, a selectable marker containing a promoter that is active only during a particular stage of the cell cycle or that is induced only when activated by a particular regulatory factor, nevertheless is considered stably expressed if the selectable marker is expressed at the appropriate time. Thus, a "stably expressed" marker is stably expressed with reference to the particular regulatory elements linked to the marker.

As disclosed herein, a MAC was obtained following irradiation of cells. A MAC also can be obtained using telomere associated chromosome truncation, which is based on the knowledge that a telomere defines the end of a chromosome (Farr et al., *EMBO J.* 14:5444–5454 (1995); Heller et al., *Proc. Natl. Acad. Sci., USA* 93:7125–2130 (1996); Brown et al., *Human Mol. Genet.* 3:1227–1237 (1994); Willard, *Proc. Natl. Acad. Sci., USA* 93:6847–6850 (1996), each of which is incorporated herein by reference). Essentially, a telomeric sequence consisting of tandem repeats of the sequence TTAGGG is inserted into chromosomal DNA. Depending on the number of telomere sequences inserted into a particular chromosome, a truncated chromosome, which contains a centromere, and one or more fragments of the chromosomal arms distal to the most centromeric insertion site are produced. Chromosomal fragments lacking centromeres ultimately are lost from the cells, whereas the truncated chromosome can be stably maintained, generally under selective pressure in a host cell.

Insertion of a telomere sequence into a chromosome can be targeted to a specific locus or can be random (see Examples III and IV). Specific targeting can be accomplished, for example, by homologous recombination into a known gene or other unique nucleic acid sequence present in the chromosome. Random insertion of telomere sequences can be accomplished using, for example, a vector containing a telomere sequence, including a linear vector containing the telomere sequence at one end.

Telomere associated chromosome truncation can be particularly useful for producing a MAC where pericentric genes or other unique pericentric nucleic acid sequences are targeted. For example, homologous recombination can be used to target a telomeric sequence to a pericentric gene such as the CII-3 gene (see Example IV). Where such targeting results in retention of the CII-3 gene in the truncated chromosome, a host cell containing the truncated chromosome can be selected based on the ability of SDH-deficient mutant cells containing the truncated chromosome to survive under the appropriate selection conditions (see Example I). It should be recognized, however, that targeted telomere associated chromosome truncation, when performed on a normal, full size chromosome, results in truncation only of the distal region of the arm containing the target site; the remaining chromosome arm generally is not affected. Thus, where site specific targeting of telomeres is used, a telomere must be introduced into a pericentric site on each arm of a selected chromosome in order to produce a useful MAC.

If desired, a telomere sequence can be linked to a nucleic acid sequence encoding a selectable marker. For example, where specific targeting of the sequence is accomplished by homologous recombination, a targeting vector comprising the telomere sequence, the sequences homologous to the target site, and the nucleic acid sequence encoding the selectable marker is introduced in the cell containing the appropriate chromosome. Following insertion of the targeting vector into the chromosome, cells containing the vector can be selected under the appropriate conditions and truncated chromosomes can be identified using routine cytogenetic methods. The inclusion of a selectable marker with the telomere sequence in a targeting vector can be particularly useful where the targeted gene such as the CII-3 gene, which otherwise is a selectable marker, is lost due to the truncation event or where the targeted pericentric sequence does not provide a means of selection or provides an inconvenient means of selection.

As disclosed herein, telomere associated truncation of a minichromosome such as a minichromosome maintained in the hybrid XJM12.1.2 and XJM12.1.3 cells (Mascarello et al., supra, 1980) or of a MAC such as MAC8.2.3 can provide significant advantages over methods of chromosome truncation previously described. For example, previous truncation methods have started with normal, full size chromosomes and have required several rounds of truncation and selection in order to obtain a minichromosome approaching a size useful as a MAC (see, for example, Heller et al., supra, 1996). However, the minichromosomes obtained following such sequential truncations contained rearrangements (see Willard, supra, 1996), which raises a question as to whether the minichromosome can function as a stably maintained entity, particularly over a long period of time. The occurrence of such rearrangements also can complicate specific targeting into the minichromosome by changing the locus, orientation or contiguity of the target site. Furthermore, even if the target site, itself, remains unaffected by a rearrangement, an unexpected level of expression of an introduced nucleic acid sequence can result due, for example, to the loss of a regulatory sequence normally associated with the target site or to the gain of a regulatory element due to the rearrangement.

In comparison to performing telomere associated chromosome truncation with normal, full size chromosomes, a stably maintained minichromosome such as the minichromosome present in XJM12.1.2 cells or in XJM12.1.3 cells provides a smaller initial target for telomere associated truncation. Thus, a truncated minichromosome useful as a MAC can be obtained after a single round of truncation and selection, limiting the probability that undesirable rearrangement of the truncated minichromosome will occur.

Similarly, a single round of telomere associated truncation can be used on a MAC such as MAC8.2.3 in order to obtain a smaller MAC, which can facilitate manipulation and transfer of the MAC (see Example IV). Specifically, a telomere sequence can be introduced into the CII-3 gene present on MAC8.2.3 by using a unique target sequence such as a sequence shown as SEQ ID NOS: 3, 5, 6 or 7 as the targeting sequence for homologous recombination. Alternatively, a telomere sequence can be introduced proximal or distal to the CII-3 gene with respect to the centromere, depending upon whether it is desired to maintain a functional CII-3 gene in the truncated MAC. As an additional advantage, targeting of a telomere sequence to the 5'-end or the 3'-end of the CII-3 gene provides a convenient means for determining the orientation and the relative position of the gene on MAC8.2.3.

A MAC can be transferred from a host cell into a second cell. For convenience, a host cell containing a MAC to be transferred is referred to herein as a "donor" cell, whereas the cell into which the MAC is transferred is referred to as a "recipient" cell. Various methods are known for transferring a MAC, which is a centromeric fragment of a chromosome, into a recipient cell. For example, a MAC can be transferred from a donor cell to a recipient cell by somatic cell fusion (see, for example, Carine et al., supra, 1986). Hybrid cells containing the MAC can be identified based on expression of the selectable marker present in the MAC. Although one or more donor cell chromosomes also will be transferred into the hybrid cells, such donor cell chromosomes generally are lost during passage of the cells because there is no selective pressure for maintaining the donor cell chromosomes in the hybrid cell. Examination of clones of hybrid cells can be used to identify hybrids containing only the MAC from the donor cells.

A host donor cell also can be treated with a mitotic spindle inhibitor such as colchicine, which results in the formation of micronuclei, then with cytochalasin B, which results in the extrusion of microcells, which contain one or a few chromosomes, including the MAC, and which can be fused to recipient cells (see, for example, Ege and Ringertz, *Expt. Cell Res.* 87:378–392 (1974); Fournier and Ruddle, *Proc. Natl. Acad. Sci., USA* 74:319–323 (1977), each of which is incorporated herein by reference. Fusion of recipient cells with microcells greatly reduces the transfer of donor cell chromosomes to recipient cells. In addition, minichromosomes can be isolated by fluorescence activated cell sorting (FACS; see Ferguson-Smith, in *Molecular Biology and Biotechnology: A comprehensive desk reference* (ed. Meyers; VCH Publ., NY; 1995) pages 354–359; Krumlauf et al., *Proc. Natl. Acad. Sci., USA* 79:2971–2975 (1982); Wallace et al., *Nucl. Acids Res.* 17:1665–1678 (1989), each of which is incorporated herein by reference). Since a MAC is much smaller than the smallest intact chromosome, isolation of MACs using FACS provides a means to obtain substantially purified MACs, which can be introduced into a recipient cell, for example, by microinjection.

A MAC containing a selectable marker is useful for stably expressing the selectable marker in a cell. A MAC containing a neo gene and a gene or cDNA encoding gene product of interest can be transferred into a diseased cell, wherein expression of the gene product complements the genetic defect and results in the cell attaining a normal phenotype. In general, a diseased cell is obtained from a patient, the MAC is transferred from a host cell into the recipient diseased cell in vitro, then the recipient cell containing the MAC is reintroduced back into the patient. Thus, a MAC can be useful as a vector for gene therapy.

In particular, a MAC is useful for introducing a large gene such as the dystrophin gene into a recipient cell because other mammalian cell vectors cannot contain such a large gene. However, a MAC is useful for introducing any gene or cDNA into a cell. Furthermore, the use of a MAC for gene therapy provides the advantage that the gene product of interest is produced in a unit dosage, since generally only a single MAC will be present in the recipient cell. In addition, a MAC is stably and autonomously maintained in each daughter cell following division of the parental cell. Thus, a MAC can be particularly useful for introducing an exogenous nucleic acid molecule into a stem cell such as a bone marrow stem cell because all the cells propagated from the stem cell will stably express the exogenous nucleic acid.

It is further recognized that a MAC is particularly useful for expressing a mammalian gene product in vitro. A MAC containing an exogenous nucleic sequence can be introduced into a mammalian cell for the purpose of expressing and collecting a mammalian gene product encoded by the nucleic acid. Mammalian cells containing a MAC can be grown in large quantities in vitro in a bioreactor under conditions that allow expression of an exogenous nucleic acid sequence contained in the MAC.

Use of a MAC to express a mammalian gene product in a mammalian cell provides significant advantages over methods for expressing the gene product in other cell types such as insect cells or bacterial cells because appropriate post-translational modifications such as glycosylation or phosphorylation of the expressed gene product can occur in a mammalian host cell. In addition, use of a MAC to introduce an exogenous nucleic acid sequence into a mammalian cell provides significant advantages over the use of other vectors. For example, the MAC is stably expressed in the mammalian cells and, therefore, is passed from generation to generation in dividing cells. In addition, a MAC is maintained as an autonomous entity in a cell and, therefore, does not integrate into the genomic DNA, where it can disrupt the regulation or expression of endogenous gene products. Thus, the present invention provides a method of producing an exogenous mammalian gene product in a cell by introducing a MAC containing an exogenous nucleic acid sequence encoding a mammalian gene product into a mammalian cell and expressing the gene product. Such a method allows in vitro production of large amounts of essentially any mammalian protein, provided the nucleic acid sequence encoding the protein is known.

A MAC also is useful for producing a transgenic mammal such as a mouse, cow, goat or sheep expressing a gene of interest (see Example V). A MAC is particularly useful for this purpose because the MAC is stably and autonomously maintained in all of the cells containing the MAC. However, it is not necessary that the exogenous nucleic acid sequence be expressed in every cell containing the MAC because expression of the exogenous nucleic acid sequence is dependent on the particular characteristics of the promoter that directs its expression. Thus, the introduction of the MAC into an embryonic stem cell or into an ovum provides a means to produce a transgenic mammal having a desirable characteristic. For example, a MAC containing a selectable marker can be microinjected into an ovum, which can fertilized at the time of microinjection or can be unfertilized, then fertilized following microinjection. The MAC-containing zygote then is implanted into a pregnant or pseudopregnant female and the newborn mammals are examined for expression of the selectable marker. Transgenic mammals expressing the selectable marker are thereby produced.

The following examples are intended to illustrate but not limit the present invention.

EXAMPLE I

Preparation and Characterization of a Mammalian Artificial Chromosome

This example provides methods for preparing and characterizing MAC-8.2.3, which is contained in XEW8.2.3 cells deposited on Oct. 31, 1995, as ATCC Accession No. ATCC CRL 11992.

The various cell lines used in this study and the hybrids derived from the fusion of the Chinese hamster mutant cells with human cells have been described previously (Mascarello, supra, 1980; Carine, supra, 1986, 1989). Briefly, CLL16-B1 is a Chinese hamster lung fibroblast from which the SDH-deficient mutant cell line CLL16-B9 was selected (Ditta et al., *Somat. Cell Genet.* 2:331–344 (1976), which is incorporated herein by reference; Soderberg et al., supra, 1977). The hybrid cell lines XJM5.1.1(+) and XJM12.1.3 were derived from the fusion of the CCL16-B9 cells with human lymphocytes or HT1080 fibrosarcoma cells (Croce, *Proc. Natl. Acad. Sci., USA* 73:3248–3252 (1976), which is incorporated herein by reference) and by selection of respiration-competent cells. The hybrid cell line XJM5.1.1(−) was a respiration-deficient segregant which had lost human chromosome 1. XJM12.1.3 was one of two independent hybrids with a human minichromosome. The secondary hybrids XEW8.2.3 and XEW9.10.4 were isolated after fusing irradiated XJM12.1.3 hybrids with CCL16-B9 cells and selecting for SDH-positive hybrids (Carine et al., supra, 1986).

All cells were grown in Dulbecco's modified Eagle's medium (DMEM) containing 5 mM glucose and 10% fetal calf serum. The same medium with glucose substituted by galactose (DME-GAL) was used to select for or maintain respiration-competent cells or hybrids (Ditta et al., supra, 1976; Scheffler et al., in *Biomedical and Clinical Aspects of Coenzyme Q*, pages 245–253 (Folders and Yamamura, eds.; Elsevier/North Holland Biomed. Press, Amsterdam; 1981), which is incorporated herein by reference).

The partial cDNA encoding the bovine heart CII-3 subunit of complex II (Yu et al., *J. Biol. Chem.* 267:24508–24515 (1992), which is incorporated herein by reference) and the complete bovine cDNA (Cochran et al., *Biochem. Biophys. Acta* 1188:162–166 (1994), which is incorporated herein by reference) were obtained. Southern blot analysis was performed on human, hamster and hybrid genomic DNA using the bovine CII-3 cDNA probe. Southern blot and northern blot analyses were performed using standard methods (Sambrook et al., supra, 1989); probes were labeled by the random primer method. Restriction enzymes were obtained from New England Biolabs (Beverly Mass.) and used according to the manufacturer's instructions. ($\alpha$-$^{32}$P)-dCTP was from ICN Pharmaceuticals (Irvine Calif.).

Southern blot analysis revealed that the (human×hamster) hybrid cells contained, in addition to the hamster chromosomes, a small number of human chromosomes. The hybrid XJM5.1.1. (+) contains an intact human chromosome 1, while the hybrid XJM5.1.1. (−) has lost the entire chromosome 1 during subsequent culture in nonselective conditions (Mascarello et al., supra, 1980). The hybrids XJM12.1.3 and XJM12.2.2 contain a human minichromosome, with a few million base pairs of DNA from the short arm of chromosome 1; the secondary hybrids XEW8.2.3 and XEW9.10.4 were derived from XJM12.1.3 after irradiation and contain a human minichromosome with 1–2 million base pairs of DNA from the short arm.

The bovine cDNA probe hybridized with hamster and with human restriction fragments even at relatively high stringency. Multiple bands were present, particularly in DNA samples obtained from the human cells. This result indicates that the human CII-3 gene consists of exons and introns or that multiple CII-3 genes or pseudogenes are present in the human genome (see Example II). Several different restriction enzymes were used in these investigations, including some that do not cleave the bovine cDNA (Xba I, Eco RI, Pst I). Interestingly, the samples from the human cells contain bands that are not present in DNA obtained from hybrids containing a human minichromosome. However, some bands are shared between total human DNA and the minichromosome present in the hybrid cells. As expected, all of the hybrid cell lines contain the band characteristic of hamster genomic DNA. These results indicate that the gene for the CII-3 subunit is found on the human minichromosome, including the minichromosome present in XEW8.2.3 cells.

In order to confirm that the genetic defect in the mutant hamster cells is due to an aberrant CII-3 gene or gene product, the ability of the bovine CII-3 cDNA to complement the SDH deficient condition of CCL16-B9 cells was examined. The complete bovine cDNA was excised from its pUC118 vector as an Eco RI fragment and cloned into the mammalian expression vector pcDNA3 (Invitrogen; San Diego Calif.) for the complementation analysis. Cells were grown to 50% confluency and transfected with the pcDNA3-CII-3 construct. As one control, pcDNA3 containing an unrelated cDNA insert was used and in a second control, no vector was added to the transfection mixture.

Transfection was performed using the "LIPO-FECTAMINE" reagent (GIBCO BRL; Grand Island Mich.); conditions for optimal transfection efficiency of the CCL16-B9 cells were established using the eukaryotic assay vector pCH110 containing the $\beta$-gal gene (Pharmacia; Piscataway N.J.). Selective medium, either DMEM containing 800 $\mu$g/ml G418, which selects for expression of the neo gene, or DMEM-galactose, which selects for respiration competent cells, was added 2 days or 4 days after transfection. After 8 days some, plates selected with G418 were switched to DMEM-galactose. Stable transfectants were maintained in DMEM-galactose containing 400 $\mu$g/ml G418.

Complementation of the defective mitochondrial function is not instantaneous because new functional complexes must be assembled in the mitochondria and time is required to accumulate levels of complex II that are adequate to support respiration and oxidative phosphorylation (Mascarello et al., supra, 1980; Carine et al., supra, 1989). Similarly, a lag period was observed in the transfected cultures when direct selection began within a few days after transfection. However, after about two weeks, cells began to divide in DMEM-galactose. In contrast, cultures that were not transfected with any vector or were transfected with the vector containing an unrelated cDNA and the neo gene, no proliferation was observed after the switch to the DMEM-galactose medium and, after a few days, the cells died and became dislodged from the plate. These results demonstrate that the bovine CII-3 cDNA complements the SDH deficiency in CCL16-B9 cells.

The ability of the bovine CII-3 cDNA to restore SDH activity in the mutant CCL16-B9 cells also was examined. SDH activity was determined using the assay of Green and Narahara (*J. Histochem. Cytochem.* 28:408–412 (1980), which is incorporated herein by reference), which measures the succinate-dependent reduction of the analogue 2-(p-iodophenyl)-3-(p-nitrophenyl)-5-phenyl tetrazolium chloride. The reaction product was quantitated spectrophotometrically after extraction with ethanol. Mitochondria were isolated by differential centrifugation as previously described (Ditta et al., supra, 1976; Soderberg et al., supra, 1977).

The activity measured in mitochondria from wild type hamster cells was inhibited almost completely by malonate, which indicates the assay is specific for SDH. Mitochondria from CCL16-B9 cells had less than 5% of the activity of wild type mitochondria. In the complemented mutants, the activity was restored to levels ranging from 30 to 50% of wild type.

These results indicate that the SDH deficiency observed in CCL16-B9 cells is due to a defect in either the CII-3 gene or the CII-3 gene product. In order to determine whether the defect was due to a mutation in the hamster CII-3 gene, hamster CII-3 cDNA was cloned. The availability of the bovine cDNA sequence allowed the design of primers for cloning the hamster CII-3 cDNA from wild type and mutant cells using a polymerase chain reaction (PCR). Computer analysis of the bovine CII-3 cDNA sequence was performed in order to avoid regions of the sequence likely to form hairpins or to dimerize. Sequences within the coding sequence were selected because the untranslated regions of the bovine and hamster sequences are more likely to have diverged.

Based on the computer search, two oligonucleotide sequences were prepared: 5'-TGCCAGCCCTACAGAGGACAACAC-3' (SEQ ID NO: 15) and 5'-CTGGAGTAAGAACACTACTTTAAACCGTCC-3' (SEQ ID NO: 16). Eventually only use of the primer corresponding to the 3'-end of the coding sequence (SEQ ID NO: 15) was successful for cloning a large portion of the CII-3 cDNA from wild type and mutant hamster cells by the 5' RACE protocol (Frohman et al., *Proc. Natl. Acad. Sci., USA* 85:8998–9002 (1988), which is incorporated herein by reference; see Example II).

Reverse transcription-PCR (RT-PCR) did not yield a product when the two specific primers were used. Thus, the 5' and 3' RACE methods were attempted. Although the 3' RACE protocol was not successful, the 5' RACE protocol resulted in isolation of PCR products that included the 5' untranslated region of hamster CII-3 mRNA and all but 9 nucleotides at the 31 end of the open reading frame. Four independent RT-PCR reactions were carried out with each of the wild type and mutant RNAs as templates. The PCR products were cloned into the pGEM-T vector (Promega; Madison Wis.) for direct sequencing. DNA sequencing was performed using the Sequenase 2.0 kit (United States Biochemical; Cleveland Ohio) and the SP6 and T7 sequencing primers, as described by manufacturer.

The nucleotide sequence of the wild type hamster CII-3 cDNA is accessible from the GenBank/EMBL Data Bank at Accession No. US1241, which is incorporated herein by reference. All of the clones obtained from mutant cells contained a G–>A transition in codon 137, resulting in the conversion of a tryptophan codon to a STOP codon. As a result of the mutation in the CII-3 cDNA, 33 amino acids normally found at the C-terminus of the translated protein are absent. A comparison of the bovine and hamster CII-3 cDNA sequences demonstrated 86% conservation at the nucleotide level and 82% conservation at the amino acid sequence level. The changes are largely conservative changes and are scattered throughout the entire peptide.

The results of these studies demonstrate that the defect in the SDH deficient CCL16-B9 hamster cell line is due to a genetic mutation at a single nucleotide in the CII-3 gene, resulting in production of a truncated CII-3 protein. In addition, the results demonstrate that the corresponding human CII-3 gene is very closely linked to the human chromosome 1 centromere. Based on these results, a unique DNA sequence has been defined on the minichromosome that is present in XEW8.2.3 cells; the minichromosome is designated herein as MAC-8.2.3.

EXAMPLE II
CII-3 cDNA and Partial Genomic DNA Sequence

This example describes methods for isolating nucleic acid sequences encoding the CII-3 subunit of complex II of the mitochondrial electron transport system.

A. Human CII-3 cDNA

A complete human cDNA encoding CII-3 was cloned from a HeLa cell cDNA library using the 5' and 3' RACE method and sequenced by the dideoxy chain termination method. The first strand cDNA library was produced by reverse transcription of 1 µg total RNA from HeLa cells using the dT17 anchor primer 5'-GACTCGAGTCGACATCGATTTTTTTTTTTTTTTT-3' (SEQ ID NO: 12) and "SUPERSCRIPT II" (RNAse H(−); BRL; Gaithersburg Md.) at 48° C., followed by poly C tailing using terminal deoxynucleotidyl transferase (BRL).

The 5'-cDNA was cloned by PCR amplification of the first strand cDNA library using a gene specific primer, 5'-GCCAGCCCCATAGAGGACAACAC-3' (SEQ ID NO: 13) and the dG15 anchor primer, 5'-GACTAGTCGACTGCAGGGGGGGGGGGGGGG-3' (SEQ ID NO: 14). The 550 base pair (bp) PCR product was cloned directly into the pGEM-T vector (Promega). The 3'-cDNA was cloned by PCR amplification of the first strand cDNA library using the gene specific primer 5'-GACTCGAGTCGACATCGATTTTTTTTTTTTTTTT-3' (SEQ ID NO: 12). The 1000 bp PCR product was cloned directly into pGEM-T.

The CII-3 cDNA contains a 27 nucleotide 5'-untranslated sequence, a 510 nucleotide coding sequence, and a 779 nucleotide 3'-untranslated sequence (SEQ ID NO: 1; see, also, GenBank Accession No. U57877). The human CII-3 amino acid sequence as deduced from SEQ ID NO: 1 is shown as SEQ ID NO: 2. Three independent clones were isolated and sequenced from the cDNA library and each contained the same CII-3 cDNA sequence. This result suggests that only a single CII-3 gene is expressed in human cells. Northern blot analysis also identified only a single band, although it is unknown whether the band corresponded to one or more RNA transcripts. Significantly, expression the cloned human CII-3 cDNA (SEQ ID NO: 1) in the SDH-deficient CCL16-B9 cells complemented the mutation, thereby allowing the cells to survive under the selective conditions (see Example I). This result confirms that the cloned human cDNA sequence encodes a functional CII-3 gene product.

B. Human CII-3 Genomic DNA Sequences

Human genomic DNA cloned in the lambda DASH vector was purchased from Stratagene (La Jolla Calif.) and screened using a bovine CII-3 cDNA (Yu et al., supra, 1992; Cochran et al., supra, 1994; see, also, Ostveen et al., *J. Biol. Chem.* 270:26104–26108 (1995), which is incorporated herein by reference). Four genomic clones containing CII-3 DNA sequences were isolated and partially characterized. One clone (JS18) contained the complete CII-3 coding sequence, with no evidence of introns. However, the coding sequence contained two in-frame stop codons and, therefore, likely represents a pseudogene. A second clone (JS5.1) also contained the complete CII-3 coding sequence, as well as sequences characteristic of a 5'- and 3'-untranslated sequence, but no introns. However, no stop codon was present in this coding sequence. Thus, it is unclear whether this sequence is expressed or is a pseudogene, although, based on the cDNA cloning, it appears that only a single CII-3 gene product is expressed.

The two remaining clones (JS2 and JS5.2) contained overlapping sequences as determined by restriction mapping. The genomic sequence in JS2 was digested with Not I and Eco RI and a 1.8 kbp NotI/EcoRI fragment was subcloned into a "BLUESCRIPT" vector (Stratagene) to produce, pJOS2 (see FIG. 2). Partial DNA sequencing of pJOS2 confirmed that the subcloned genomic sequence contained a sequence (SEQ ID NO: 4; see FIG. 2, "Exon-A") that is identical to a portion of the cloned human CII-3 cDNA (SEQ ID NO: 1).

Figure 2:
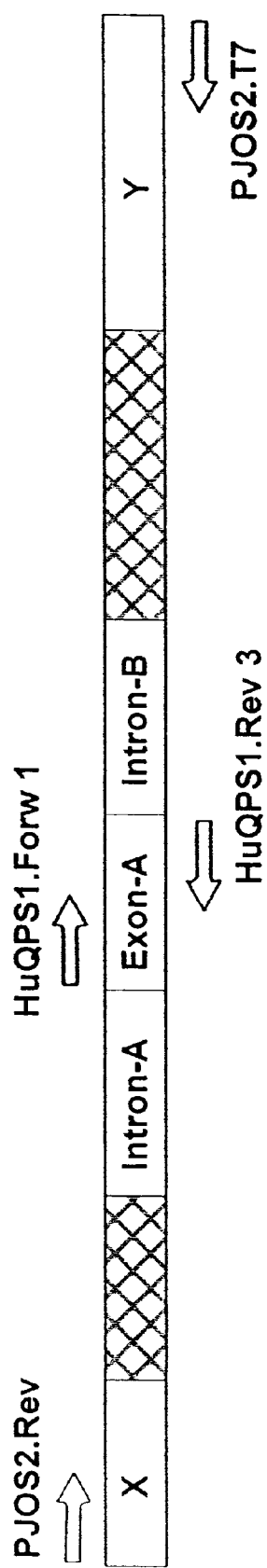
FIG. 2 provides a schematic representation of the genomic CII-3 DNA sequence cloned in pJOS2. "Intron-A" (SEQ ID NO: 3), "Exon-A" (SEQ ID NO: 4) and "Intron-B" (SEQ ID NO: 5) are indicated. "X" (SEQ ID NO: 6) and "Y" (SEQ ID NO: 7) also are indicated. "pJOS2.Rev" (SEQ ID NO: 8), "pJOS2.T7" (SEQ ID NO: 9), HuQPS1.Forw1" (SEQ ID NO: 10) and "HuQPS1.Rev3" (SEQ ID NO: 11) indicate the location of primers and the associated arrows indicate the direction of synthesis from the primer. "Hatching" indicates that the length and sequence of the genomic DNA has not yet been determined. The subclone is shown with the 5'-end at the left and the 3'-end at the left, with respect to the coding sequence of Exon-A (see SEQ ID NO: 1), and is approximately to scale, except for size and position of the hatched regions.

A portion of the subcloned genomic sequence is disclosed herein as Intron-A (SEQ ID NO: 3; 257 bp), Exon-A (SEQ ID NO: 4; 164 bp) and Intron-B (SEQ ID NO: 5; 173 bp; see, also, FIG. 2). Exon-A (SEQ ID NO: 4), which corresponds to nucleotides 268 to 431 of the human CII-3 cDNA (SEQ ID NO: 1), is bordered on its 5'-end by Intron-A (SEQ ID NO: 3) and on its 3'-end by Intron-B (SEQ ID NO: 5). Additional sequences bordering the 5-end (SEQ ID NO: 6; 261 bp) and 3'-end (SEQ ID NO: 7; 333 bp) of the 1.8 kbp genomic DNA fragment in pJOS2 also have been determined (FIG. 2; "X" and "Y," respectively). The exon and introns are referred to by letters because the complete structure of the human CII-3 gene has not yet been determined. The sequences shown as SEQ ID NOS: 5 and 6 are referred to as "X" and "Y," respectively, since it is not clear whether they constitute intron or exon sequences or portions of both. Reference to the "5'-end" and "3'-end" indicate the position relative to the reading frame encoded by Exon-A, based on its identity to the human CII-3 cDNA (SEQ ID NO: 1).

DNA sequencing was performed using the following primers: pJOS2.Rev, 5'-TGGTGAAACCCTGTCTCTAC-3' (SEQ ID NO: 8); pJOS2.T7, 5'-TCTATGCCTTCAGGGATCTC-3' (SEQ ID NO: 9); HuQPS1.Forw1, 5'-ACTTGTGAAGTCCCTGTGTC (SEQ ID NO: 10); and HuQPS1.Rev3, 5'-AAGTGTCGGATCCCATTCCA-3' (SEQ ID NO: 11). The pJOS2.Rev and pJOS2.T7 primers were prepared based on sequences of the genomic subclone that were obtained using the "universal" T7 and reverse primers specific for the cloning vector. The HuQPS1.Forw1 and HuQPS1.Rev3 primers were designed based on the human CII-3 cDNA sequence (SEQ ID NO: 1).

The HuQPS1.Forw1 and pJOS2.T7 primers, which are complementary to sequences of Exon-A and "Y," respectively (see FIG. 2), also were used to amplify genomic DNA obtained from human HeLa cells; hamster B9 cells; XJM5.1.1(+) cells, which are hamster cells containing a complete human chromosome 1 (see Example I); XJM5.1.1 (−) cells, which are derived from XJM5.1.1(+) cells that have lost the human chromosome 1; or XEW8.2.3 cells, which are hamster cells containing MAC8.2.3. The amplification products were separated by polyacrylamide gel electrophoresis and visualized by ethidium bromide staining and ultraviolet irradiation. A band migrating at about 1.05 kbp, which is the expected size of the amplified portion of the human CII-3 gene, was obtained from genomic DNA obtained from the HeLa cells, XJMS.1.1(+) and XEW8.2.3 cells, whereas no band was observed following amplification of the hamster B9 cells or the XJM5.1.1(−) cells. These results indicate that the cloned human genomic CII-3 sequences are present on chromosome 1, including on the portion of chromosome 1 comprising MAC8.2.3.

The complete human CII-3 gene readily can be determined by subcloning positive lambda genomic clones that have been isolated but not yet characterized. In addition, the complete human CII-3 gene can be obtained by rescreening the lambda DASH library to identify additional clones containing CII-3 sequences. In addition, a genomic library of XEW8.2.3 cells, including MAC-8.2.3, can be prepared and screened for genomic CII-3 sequences using the available cloned human genomic or cDNA CII-3 sequences (see Au et al., Gene 159: 249–253 (1995), which is incorporated herein by reference). Portions of the human CII-3 gene sequences present in pJOS2 or the human CII-3 cDNA (SEQ ID NO: 1) can be used as probes to screen the library.

If the human CII-3 gene cannot be characterized completely from lambda genomic clones, a yeast artificial chromosome (YAC) or a "bacterial artificial chromosome" (BAC) containing the human CII-3 gene can be purchased from Genome Systems, Inc. (St. Louis Mo.). Essentially, the manufacturer is provided with specific primers or a unique sequence to use as a probe. A sequence such as that shown as SEQ ID NO: 3, 5, 6 or 7 is ideal for this purpose, since these sequences do not encompass a coding region or regulatory region. The manufacturer then screens a BAC or YAC library, identifies a BAC or a YAC containing complementary sequences, and provides the YAC or BAC, the insert of which can be subcloned and characterized using routine methods.

Positive clones are selected and redundant clones are identified by restriction mapping. Unique clones are isolated, subclones are prepared, and the DNA sequences are determined. Overlapping sequences are identified and used to construct the entire human CII-3 gene sequence. This method allows the identification and isolation of isogenic sequences useful for targeted integration by homologous recombination (Ten Riele et al., Proc. Natl. Acad. Sci., USA 89:5128–5132 (1992), which is incorporated herein by reference).

To identify additional exons and, if present, introns, a combination of restriction mapping and partial sequencing is performed using the available cloned sequences as a probe. Putative unique sequences are examined by Southern blot analysis, comparing human genomic DNA and genomic DNA obtained from XEW8.2.3 cells. In particular, genomic sequences encoding the promoter and a portion of exon 1 will be identified.

EXAMPLE III

Modification of MAC-8.2.3

This example describes methods for introducing an exogenous nucleic acid sequence into MAC-8.2.3.

An exogenous nucleic acid sequence can be introduced into MAC-8.2.3 using homologous recombination (Ayares et al., supra, 1986; Capecchi, supra, 1989). Briefly, a construct is made containing the exogenous nucleic acid sequence of interest flanked on either side by nucleic acid sequences encoding the human CII-3 gene. In particular, unique sequences such as those identified, for example, as SEQ ID NOS: 3, 5, 6 and 7 are used such that the exogenous nucleic acid sequence is targeted to a specific locus (see FIG. 1A). Other unique sequences of the human CII-3 gene obtained as described in Example II also can be used to specifically target an exogenous nucleic acid sequence such as a selectable marker, a loxP site or a telomere sequence to the 5'-end or 3'-end of the human CII-3 gene, including at the site of human CII-3 promoter if it is desired that the exogenous nucleic acid sequence be expressed from the CII-3 gene promotor. Depending on the insertion site of the targeted sequence, CII-3 gene function can be disrupted, if desired.

An introduced exogenous nucleic acid sequence can be a loxP sequence or an FLP sequence. The introduction of such a site into MAC-8.2.3 and, in particular, into the CII-3 gene present in MAC-8.2.3 provides a means to readily introduce subsequent exogenous nucleic acid sequences into MAC-8.2.3 in a site specific manner using the Cre recombinase from bacteriophage P1 or the FLP recombinase from S. cerevisiae, respectively. A loxP site, for example, is introduced into the CII-3 gene present on MAC-8.2.3. The loxP site is introduced by transfection of a targeting vector containing the neo gene and promoter, flanked by two loxP sites, which, in turn, are flanked by human CII-3 gene sequences containing the CII-3 promoter on one side and CII-3 gene exon or intron sequences on the other side, which further is extended by the HSV-tk gene sequence (see FIG. 1A).

The gene encoding puromycin resistance also can be incorporated into the targeting vector, either in place of or in addition to another selectable marker such as neo (Skerjanc et al., Mol. Cell. Biol. 14:8451–8459 (1994); Vara et al., Nucl. Acids Res. 14:4617–4624 (1986), each of which is incorporated herein by reference). Use of the puromycin gene has advantages over the neo gene because puromycin is significantly less expensive than G418. Also, the cDNA encoding the green fluorescent protein (GFP) can be used as a selectable marker (see Yeh et al., Proc. Natl. Acad. Sci., USA 92:7036–7040 (1995), which is incorporated herein by reference). GFP is particularly useful as a selectable marker because cells expressing GFP can be identified and, if desired, isolated using a fluorescence activated cell sorter (FACS).

Following transfection of the host cells with the targeting vector, cells are grown in medium containing G418 and gancyclovir. Cells that grow in this medium express the neo gene, but do not express the HSV-tk gene and, therefore, are considered to have incorporated the targeting vector by homologous recombination into the human CII-3 gene (see FIG. 1B). Targeted integration is confirmed using PCR. This method produces MAC-(loxP-neo-loxP), which contains an active neo gene, flanked by loxP sites, integrated downstream of the promoter of the CII-3 gene.

Mammalian cells containing MAC-(loxP-neo-loxP) are transfected with a vector expressing the Cre gene, wherein transient expression of the Cre gene results in precise and efficient excision of the neo gene, leaving a single loxP site in the untranslated portion of exon I (see FIG. 1C) and producing MAC-(loxP). Similarly, the purified Cre protein can be introduced directly into MAC-1-containing cells using lipofection (Baubonis and Sauer, supra, 1993). Precise excision of the neo gene is confirmed by PCR. MAC-(loxP) contains a single loxP site useful for targeting an exogenous nucleic acid sequence.

A promoterless neo gene can be introduced into MAC-8.2.3 such that a transcript produced therefrom contains the upstream portion of exon 1 and the loxP sequence, which forms the 5' untranslated region of the neo transcript (see Jeannotte et al., Mol. Cell. Biol. 11:5578–5585 (1991); Charron et al., Mol. Cell. Biol. 10:1799–1804 (1990); Schwartzberg et al., Proc. Natl. Acad. Sci., USA 87:3210–3214 (1990), each of which is incorporated by reference). If desired, the translation start site of the CII-3 gene, which encodes the portion of the polypeptide that targets it to the mitochondria, can be deleted.

Cells carrying a single loxP site on the minichromosome are cotransfected with a circular targeting vector containing an exogenous nucleic acid sequence and a second loxP site (see FIG. 1D) and with an expression vector containing the Cre recombinase gene. Recombinase-mediated integration of the vector at the loxP site in the MAC inserts the exogenous nucleic acid sequence into the MAC (see FIG. 1E). The loxP sites are oriented, with respect to each other, so as to yield the desired orientation of the introduced sequence. The targeting vector can contain a promoterless cDNA sequence, which, following specific integration, is expressed from the CII-3 promoter. In addition, the targeting vector can contain a neo gene, with promoter, to allow selection. Alternatively, the neo gene can be promoterless and can be separated from the exogenous nucleic acid sequence by a short sequence, including an internal ribosome entry site, IRES, (see FIG. 1D; Mountford and Smith, Trends Genet. 11:179–184 (1995), which is incorporated herein by reference). The CII-3 promoter directs expression of a dicistronic mRNA and neo resistance occurs only following specific integration.

A MAC containing a dominant selectable marker can be transferred into a variety of mammalian cells and cells containing the MAC can be identified. Selection for G418 resistance or puromycin resistance is powerful and allows the identification of cells containing the MAC even where there is a low efficiency of transfer. A MAC can be introduced into a mammalian recipient cell by somatic cell fusion with a host donor cell such as XEW8.2.3, which contains the MAC (Carine et al., supra, 1986).

Prior to fusion, the host cell containing the MAC can be irradiated at a dose that fragments the host cell chromosomes, such as the hamster chromosomes in XEW8.3.2, but spares the MAC, which is not hit due to its small size. The irradiated host cells then are fused to a mammalian cell line such as COS cells (monkey), 3T3 cells (mouse), or other cells including human cells or mouse embryonic stem (ES) cells and cells that grow under the appropriate selection conditions are obtained.

EXAMPLE IV
Method of Reducing the Size of a MAC

This example describes methods for producing a MAC or for reducing the size of a MAC such as MAC8.2.3.

A MAC can be produced by irradiation of normal chromosomes or minichromosomes at a dose that results in their fragmentation. Similarly, irradiation can be used to reduce the size of a MAC such as MAC8.2.3. For example, host cells containing MAC8.2.3 can be exposed to a dose that results in the MAC being hit one or a few times. Such a method was used to obtain MAC-8.2.3 from hybrid cell line XJM12.2.3, which contains a larger MAC, and can be used, if desired, to select a MAC that is smaller than MAC-8.2.3. Alternatively, by randomly inserting a selectable marker in the genome of a cell, fragmenting the chromosomes, and fusing the cell with an intact cell, neomycin resistant hybrids can be obtained. By screening the resistant hybrids using the methods disclosed herein, a new MAC having a neo gene inserted in a pericentric location can be obtained.

Fragmentation of chromosomes, minichromosomes or a MAC using telomerase associated truncation also can be used to produce a MAC or reduce the size of a MAC. For example, a telomere sequence consisting of repeated units of the sequence TTAGGG can be introduced into the region of the CII-3 gene present on MAC8.2.3 such that sequences distal to the telomere with respect to the centromere are lost from the MAC.

Site specific targeting of a telomere sequence is accomplished by homologous recombination using a targeting vector as described in Example III, except that the telomere sequence is substituted, for example, for the loxP site. Of course, if a loxP site first is placed into MAC8.2.3, the telomere sequence can be introduced into the site by incorporating the sequence into an appropriate vector (see FIG. 1E), introducing the vector into a host cell containing MAC8.2.3 and expressing the Cre recombinase in the cell (see Example III). The sequences in the targeting vector for directing an exogenous nucleic acid sequence into MAC8.2.3 by homologous recombination can be, for example, those disclosed herein as SEQ ID NOS: 3, 5, 6 or 7, since these sequences likely are unique sequences in the human genome and, therefore, in MAC8.2.3. The use of such unique sequences will preclude insertion of the targeting vector into the hamster chromosomes present in the host XEW8.2.3 cells.

EXAMPLE V
Production of Transgenic Mice

This example provides a method for producing transgenic mice by stably expressing a MAC containing a selectable marker in the mice.

Transgenic mice are created by introducing a MAC containing an exogenous nucleic acid sequence into embryonic stem (ES) cells, then microinjecting the ES cells into mouse embryos. Methods for culturing ES cells are well known in the art (see, for example, Kriegler, supra, 1990). Briefly, superovulation is induced by intraperitoneal injection of hormones using a 27G1/2 needle to deliver less than 200 µl hormone and the mice are mated. The pregnant females are anesthetized by inhalation with Metafane and sacrificed by cervical dislocation and fertilized embryos are removed from the oviduct. ES cells containing a MAC are selected and microinjected into the embryos. Alternatively, a MAC is microinjected into an ovum, which is fertilized. Pseudopregnant females are anesthetized by inhalation with Metafane and the embryos or fertilized ova are implanted into the oviduct. Offspring, which are weaned at three or more weeks of age, are anesthetized by inhalation with Metafane, one half inch of tail is removed using a sterile blade and a blood sample is obtained. DNA is isolated from the blood sample and screened by Southern blot analysis to identify animals containing the exogenous nucleic acid.

Although the invention has been described with reference to the examples provided above, it should be understood that various modifications can be made without departing from the spirit of the invention. Accordingly, the invention is limited only by the claims.

What is claimed is:

1. A method of producing a mouse expressing a selectable marker which is present on a mammalian artificial chromosome (MAC), comprising the steps of:
   a. introducing a MAC containing the selectable marker into an ovum cell, said ovum cell fertilized into a zygote at the time of or following said introduction of said MAC, wherein said zygote contains said MAC containing said selectable marker;
   b. implanting said MAC-containing zygote into a female mammal; and
   c. selecting a mouse produced from said zygote, wherein said mouse expresses said selectable marker.

2. A method of producing a mouse expressing a selectable marker which is present on a mammalian artificial chromosome (MAC), comprising the steps of:
   a. introducing a MAC containing the selectable marker into an embryonic stem cell;

b. introducing said MAC-containing embryonic stem cell into an embryo;

c. implanting said MAC-containing embryo into a female mammal; and d. selecting a mouse produced from said embryo, wherein said mouse expresses said selectable marker.

3. The method of claim wherein said MAC is less than about 0.1% of the size of the normal haploid genome of the mammalian cell from which the centromere was obtained.

4. The method of claim 1, wherein said MAC comprises a unique cloning site, which comprises a nucleic acid sequence encoding said selectable marker.

5. The method of claim 1, wherein said selectable marker is an exogenous nucleic acid sequence.

6. The method of claim 2, wherein said MAC is less than 0.1% of the size of the normal haploid genome of the mammalian cell from which the centromere was obtained.

7. The method of claim 2, wherein said MAC comprises a unique cloning site, which comprises a nucleic acid sequence encoding said selectable marker.

8. The method of claim 2, wherein said selectable marker is an exogenous nucleic acid sequence.

9. A method of producing a transgenic mouse expressing a selectable marker which is present on a mammalian artificial chromosome (MAC), comprising the steps of:

a. introducing a MAC containing the selectable marker into an embryonic stem cell by microcell fusion of an embryonic stem cell and a second cell which contains the MAC to produce a hybrid cell expressing the selectable marker;

b. introducing said MAC-containing hybrid cell into an embryo;

c. implanting said MAC-containing embryo into a female mammal;

d. selecting a mouse produced from said embryo, wherein germ cells of said mouse express said selectable marker;

f. mating said mouse with another mouse to produce progeny; and g. selecting a transgenic mouse from said progeny.

10. The method of claim 9, further comprising selecting said hybrid cell by culturing hybrid cells under conditions to select for expression of the selectable marker.

11. The method of claim 9, wherein said MAC comprises a unique cloning site.

12. The method of claim 11, wherein said unique cloning site comprises a nucleic acid sequence encoding said selectable marker.

13. The method of claim 9, wherein said MAC is less than 0.1% of the size of the normal haploid genome of the mammalian cell from which the centromere was obtained.

14. The method of claim 9, wherein said selectable marker is an exogenous nucleic acid sequence.

* * * * *